(12) United States Patent
Allmendinger et al.

(10) Patent No.: US 10,251,613 B2
(45) Date of Patent: Apr. 9, 2019

(54) X-RAY CT SCANNING AND DUAL-SOURCE CT SYSTEM

(71) Applicant: Siemens Healthcare GmbH, Erlangen (DE)

(72) Inventors: Thomas Allmendinger, Forchheim (DE); Johan Sunnegardh, Erlangen (DE)

(73) Assignee: SIEMENS HEALTHCARE GMBH, Erlangen (DE)

(*) Notice: Subject to any disclaimer, the term of this patent is extended or adjusted under 35 U.S.C. 154(b) by 142 days.

(21) Appl. No.: 15/297,405

(22) Filed: Oct. 19, 2016

(65) Prior Publication Data

US 2017/0035375 A1 Feb. 9, 2017

Related U.S. Application Data

(63) Continuation-in-part of application No. 14/183,579, filed on Feb. 19, 2014, now Pat. No. 9,498,168.

(30) Foreign Application Priority Data

Mar. 1, 2013 (DE) .................. 10 2013 203 541

(51) Int. Cl.
*A61B 6/00* (2006.01)
*A61B 6/03* (2006.01)
(Continued)

(52) U.S. Cl.
CPC .............. *A61B 6/032* (2013.01); *A61B 6/035* (2013.01); *A61B 6/06* (2013.01); *A61B 6/4014* (2013.01); *A61B 6/482* (2013.01); *A61B 6/0457* (2013.01)

(58) Field of Classification Search
CPC ......... A61B 6/027; A61B 6/032; A61B 6/035; A61B 6/482; A61B 6/2014; A61B 6/4028;
(Continued)

(56) References Cited

U.S. PATENT DOCUMENTS 6,118,839 A 9/2000 Dafni et al.
6,580,777 B1 6/2003 Ueki et al.
(Continued)

FOREIGN PATENT DOCUMENTS

CN 1433282 A 7/2003
CN 1663533 A 9/2005
(Continued)

OTHER PUBLICATIONS

Morneburg H.; "Bildgebende Systeme für die medizinische Diagnostik"; Publicis MCD Verlag; 3. wesenflich überarbeitete and erweiterte Auflage; pp. 254-261; ISBN: 3-89578-0022; 1995.
(Continued)

*Primary Examiner* — Phillip A Johnston
*Assistant Examiner* — Hsien Tsai
(74) *Attorney, Agent, or Firm* — Harness, Dickey & Pierce, P.L.C.

(57) ABSTRACT

A method is disclosed for x-ray CT scanning with a dual-source system, in which two radiation bundles are each delimited by diaphragms such that these radiation bundles are free of mutual points of intersection at least in the examination object. An embodiment of the invention also relates to a dual source CT system, including a controller configured to control radiation-delimiting diaphragms, which delimit and align the radiation bundles such that these run free of mutual points of intersection at least in the examination object.

14 Claims, 17 Drawing Sheets

(51) Int. Cl.
*A61B 6/06* (2006.01)
*A61B 6/04* (2006.01)

(58) Field of Classification Search
CPC ... A61B 6/4035; A61B 6/4007; A61B 6/4241; A61B 6/4488; G01N 23/046; G01N 2223/419
See application file for complete search history.

(56) References Cited

U.S. PATENT DOCUMENTS

| | | | |
|---|---|---|---|
| 7,187,748 B2 | 3/2007 | Hoffman | |
| 7,203,268 B2 | 4/2007 | Yahata | |
| 7,627,081 B2 | 12/2009 | Bantus | |
| 7,945,012 B2 | 5/2011 | Ye et al. | |
| 8,576,981 B2* | 11/2013 | Hagiwara | G06T 11/006 378/15 |
| 2003/0108146 A1* | 6/2003 | Malamud | A61B 6/032 378/19 |
| 2004/0081270 A1 | 4/2004 | Heuscher | |
| 2005/0195935 A1 | 9/2005 | Yahata | |
| 2007/0290138 A1 | 12/2007 | Scholz | |
| 2010/0091940 A1 | 4/2010 | Ludwig et al. | |
| 2011/0075809 A1* | 3/2011 | Boese | A61B 6/032 378/92 |

FOREIGN PATENT DOCUMENTS

| | | |
|---|---|---|
| DE | 102006027221 A1 | 12/2007 |
| JP | 2007007217 A | 1/2007 |

OTHER PUBLICATIONS

German Office Action for German Application 10 2013 203 541.1 dated Nov. 11, 2013.
German Priority Document German Application 10 2013 203 541.1 Filed Mar. 1, 2013.
Office Action for Chinese Patent Application No. 201410071926.X dated Nov. 3, 2016 and English translation thereof.

* cited by examiner

X-RAY CT SCANNING AND DUAL-SOURCE CT SYSTEM

PRIORITY STATEMENT

The present application is a continuation-in-part under 35 U.S.C. § 120 of U.S. patent application Ser. No. 14/183,579, filed on Feb. 19, 2014, which claims priority under 35 U.S.C. § 119 to German patent application number DE 102013203541.1 filed Mar. 1, 2013, the entire contents of each of which are hereby incorporated herein by reference.

FIELD

At least one embodiment of the invention generally relates to x-ray CT scanning of an examination object with two emitter-detector systems arranged at different angles on a shared gantry of a CT system, wherein each emitter has a focal point and each detector is embodied as a multi-row detector having a scattered radiation grid operating in a two-dimensional manner, and during the scanning process between each focal point and the opposing detector of each emitter-detector system, a radiation bundle diverging in two dimensions and delimited by emitter-side diaphragms is generated.

Furthermore, at least one embodiment of the invention also generally relates to a dual-source CT system for scanning an examination object, comprising two emitter-detector systems arranged at different angles on a gantry with, in each instance, at least one x-ray tube, which forms a focal point during operation, which rotates on a peripheral line about a system axis running in the z-direction, and a multi-row detector likewise rotating about the system axis, the detector rows of which run in the peripheral direction, having a scattered radiation grid operating in a two-dimensional manner, wherein, based on the respective focal point, a radiation bundle delimited by diaphragms is aligned toward the respectively assigned multi-row detector.

Furthermore, at least one embodiment of the invention generally relates to x-ray CT scanning of an examination object with two emitter-detector systems arranged at different angles on a shared gantry of a CT system, wherein each emitter has a focal point and each detector is embodied as a multi-row detector having a scattered radiation grid operating in a two-dimensional manner, and during the scanning process between each focal point and the opposing detector of each emitter-detector system, a radiation bundle diverging in two dimensions is generated and wherein, a displacement apparatus is provided for at least one emitter-detector system, which is configured to displace at least one emitter-detector system in the z-direction.

BACKGROUND

A method and a dual-source CT system used for this purpose are generally known. With such scanning methods and such CT systems having two tubes in a 90° arrangement, operation in the dual tube mode inevitably results in the development of transverse scatter on the object, which, for geometric reasons, can also not be screened out by a scattered radiation grid operating in a two-dimensional manner across the detectors and is therefore measured on the detector as an additional signal. If the amounts of this transverse scatter are not corrected, this inevitably results in artifacts in the image, which, particularly during a two spectra dual-source scan, in other words during dual-energy operation, have a sustained adverse effect on the evaluation and deliver artifact-loaded results.

For this reason, algorithms have been developed, which attempt to estimate and correct these scattered radiation amounts. Technical hardware solutions also exist for measuring and correcting the scattered radiation amounts, such as for instance scatter monitors, reduced collimation for measuring the scattered radiation amounts in the edge lines. In particular, the recording modes based on edge line correction were used in previously existing devices to deliver high-quality results.

For a device with a scattered radiation grid operating in a two-dimensional manner, this type of data acquisition and correction is however not possible.

SUMMARY

At least one embodiment of the invention is directed to a method and/or an x-ray CT scanning with two emitter-detector systems and a dual-source CT system which, during the scanning process, have a reduced tendency toward the formation of artifacts in the CT displays produced therefrom.

Advantageous developments of the invention are the subject matter of subordinate claims.

The inventor has identified that a special form of data acquisition and control of the scanning radiation bundle may allow for extensive suppression of the scattered radiation amounts. The key to this is an asymmetric operation of the two detectors with respect to the superimposed rows, which, in combination with the two-dimensional scattered radiation grid, result in a strong suppression of the scattered radiation amounts in the respective other detector. This is effected by guidance of the scanning beams such that the radiation bundle of both emitter-detector systems no longer has points of intersection.

To this end, a CT system is developed in at least one embodiment, in which the detector systems and/or the focal points of the emitter are offset relative to one another in the z-direction to such a degree that, despite using a shared gantry, overlaps are prevented between the two radiation bundles of the emitter-detector systems. As a result, the appearance of scattered radiation in the radiation path of the one emitter-detector system is prevented by radiation from the respective other emitter-detector system. The other scattered radiation essentially always produced in both systems can then be suppressed by scattered radiation grids operating in a two-dimensional manner, when considered purely geometrically and in a first approximation. The advantage of such an embodiment of a CT system lies in the used multi-row detectors being able to be used over their entire surface. Nevertheless, this advantage is thus gained in that a simultaneous scanning of a region is no longer possible by two radiation bundles only disposed at different angles.

The inventor proposes improving an x-ray CT scanning of an examination object with two emitter-detector systems arranged at different angles on a shared gantry of a CT system, wherein each emitter has a focal point and each detector is embodied as a multi-row detector having a scattered radiation grid operating in a two-dimensional manner, and during the scanning process between each focal point and the opposing detector of each emitter-detector system, a radiation bundle diverging in two dimensions and delimited by emitter-side diaphragms is generated. In accordance with at least one embodiment of the invention, the two radiation bundles are to be delimited by the diaphragms respectively such that these radiation bundles are free of mutual points of intersection, at least in the examination object.

Finally, a method is disclosed. In at least one embodiment includes a method of X-ray CT scanning of an examination object using two emitter-detector systems arranged at different angles on a shared gantry of a CT system, each of the two emitters including a focal point and each of the two detectors being embodied as a multi-row detector with a scattered radiation grid operating in a two-dimensional manner, the method comprising:

generating, during the scanning process between each of the respective focal points and an opposing one of the two detectors of each of the two emitter-detector systems, a radiation bundle diverging in two dimensions and delimited by emitter-side diaphragms, wherein the two radiation bundles are delimited by the diaphragms, respectively, such that the radiation bundles are free of mutual points of intersection at least in the examination object.

The inventor has identified that a special form of data acquisition and control of the position of the emitter-detector systems relative to each other may allow for adaption of an axial collimation and/or reduction of forward scatter and cone beam artefacts. The key to this is a displaced operation of the two emitter-detector systems relative to each other, which may result in a suppression of the forward scatter and cone beam artefacts, at least during or after reconstruction. This may be effected by displacing of the emitter-detector systems such that the helical or circular paths of both emitter-detector systems run on an identical line or shifted by 180°. Furthermore, a large shift may suppress cross-scatter and even mutual points of intersection at least in the examination object.

The inventor proposes improving an x-ray CT scanning of an examination object with two emitter-detector systems arranged at different angles on a shared gantry of a CT system, wherein each emitter has a focal point and each detector is embodied as a multi-row detector having a scattered radiation grid operating in a two-dimensional manner, and during the scanning process between each focal point and the opposing detector of each emitter-detector system, a radiation bundle diverging in two dimensions and wherein the emitter-detector systems are displaced. In accordance with at least one embodiment of the invention, the shift of the emitter-detector system is adapted to the pitch.

A further method is disclosed. In at least one embodiment includes a method of X-ray CT scanning of an examination object using two emitter-detector systems arranged at different angles on a shared gantry of a CT system, each of the two emitters including a focal point and each of the two detectors being embodied as a multi-row detector with a scattered radiation grid operating in a two-dimensional manner, the method comprising:

selecting an offset and moving at least one emitter-detector system A and/or B by the offset along a system axis, generating, during the scanning process between each of the respective focal points and an opposing one of the two detectors of each of the two emitter-detector systems, a radiation bundle diverging in two dimensions and acquiring an image for each of the two detectors.

A further dual-source CT system for scanning an examination object is disclosed, comprising:

two emitter-detector systems, arranged at different angles on a gantry, each including at least one x-ray tube which forms a respective focal point during operation and which is configured to rotate on a peripheral line about a system axis running in the z-direction, and a multi-row detector, configured to rotate about the system axis, detector rows of the multi-row detector being configured to run in the peripheral direction, the multi-row detector including a scattered radiation grid configured to operate in a two-dimensional manner, wherein, based on a respective focal point, wherein, a displacement apparatus is provided for at least one emitter-detector system, which is configured to displace at least one emitter-detector system in the z-direction.

In a further embodiment, the dual-source CT system provides at least one displacement apparatus for at least one emitter-detector system, which is configured to displace the at least one emitter-detector system in the z-direction.

BRIEF DESCRIPTION OF THE DRAWINGS

The invention is described in more detail below on the basis of preferred example embodiments with the aid of the figures, wherein only the features required to understand the invention are shown. The following reference signs are used: 1: CT system; 2: x-ray tube; 2.1: controllable diaphragm; 2.2: focal point; 3: multi-row detector; 4: x-ray tube; 4.1: controllable diaphragm; 4.2: focal point; 5: multi-row detector; 6: gantry housing; 7: examination object; 8 patient couch; 9: system axis; A, B: emitter-detector system; D: detector; G: scattered radiation grid; K tilting apparatus; M: center line of the detectors; Prg1-Prgn: computer programs; R: x-ray tube; RA: anode; RB: diaphragm; RF: focus; S,SA,SB: radiation bundle/beam cone; UM, U', U": peripheral lines; V: displacement apparatus; κ: tilting angle.

In detail.

DETAILED DESCRIPTION OF THE EXAMPLE EMBODIMENTS

Figure 1:
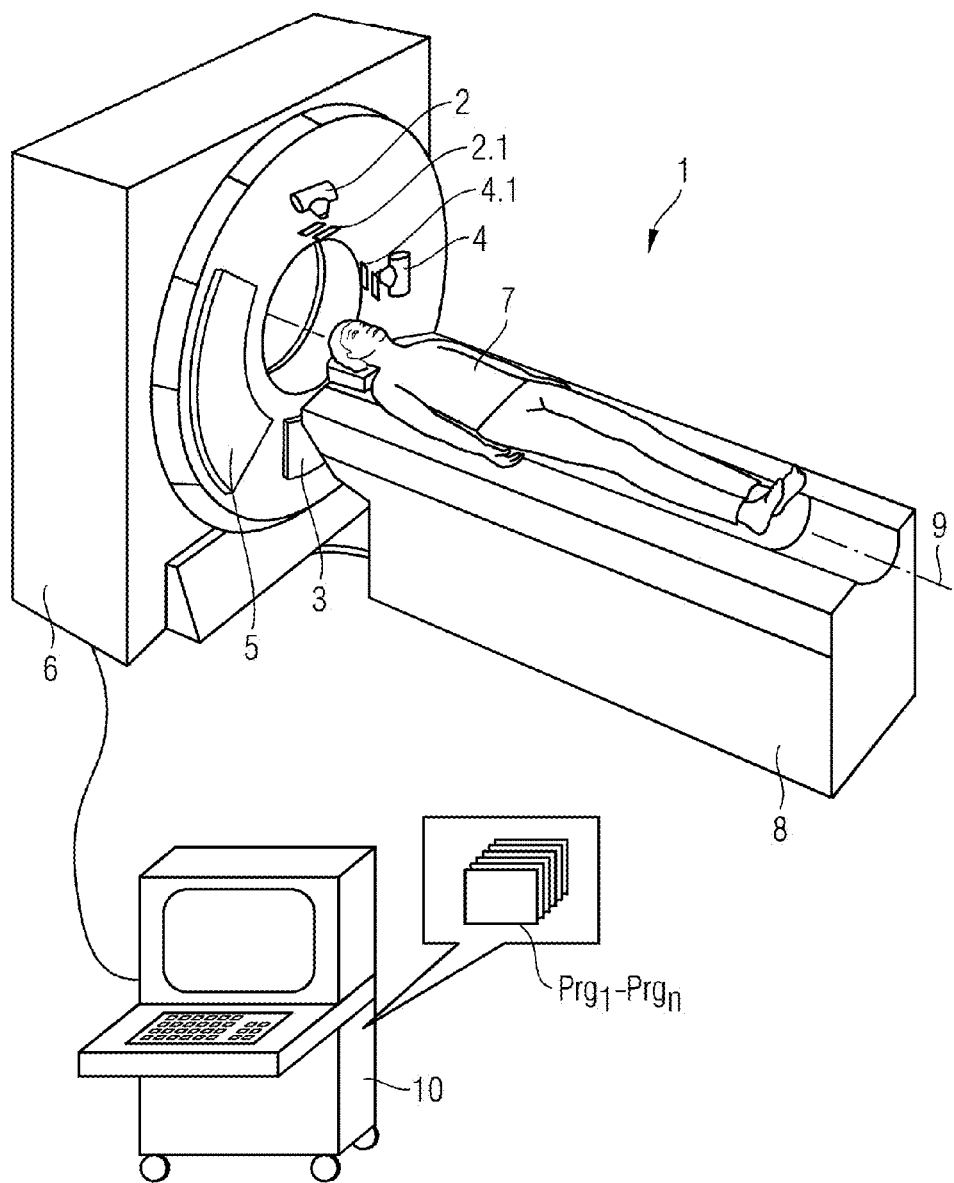
FIG. 1 shows a dual-source CT system

The present invention will be further described in detail in conjunction with the accompanying drawings and embodiments. It should be understood that the particular embodiments described herein are only used to illustrate the present invention but not to limit the present invention.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The inventor has identified that a special form of data acquisition and control of the scanning radiation bundle may allow for extensive suppression of the scattered radiation amounts. The key to this is an asymmetric operation of the two detectors with respect to the superimposed rows, which, in combination with the two-dimensional scattered radiation grid, result in a strong suppression of the scattered radiation amounts in the respective other detector. This is effected by guidance of the scanning beams such that the radiation bundle of both emitter-detector systems no longer has points of intersection.

To this end, a CT system is developed in at least one embodiment, in which the detector systems and/or the focal points of the emitter are offset relative to one another in the z-direction to such a degree that, despite using a shared gantry, overlaps are prevented between the two radiation bundles of the emitter-detector systems. As a result, the appearance of scattered radiation in the radiation path of the one emitter-detector system is prevented by radiation from the respective other emitter-detector system. The other scattered radiation essentially always produced in both systems can then be suppressed by scattered radiation grids operating in a two-dimensional manner, when considered purely geometrically and in a first approximation. The advantage of such an embodiment of a CT system lies in the used multi-row detectors being able to be used over their entire surface. Nevertheless, this advantage is thus gained in that a simultaneous scanning of a region is no longer possible by two radiation bundles only disposed at different angles.

The inventor also proposes at least one embodiment directed to a dual-source CT system for scanning an examination object, comprising two emitter-detector systems arranged at different angles on a gantry with, in each instance, at least one x-ray tube, which forms a focal point during operation, which rotates on a peripheral line about a system axis running in the z-direction, and a multi-row detector likewise rotating about the system axis, the detector rows of which run in the peripheral direction, having a scattered radiation grid operating in a two-dimensional manner, wherein, based on the respective focal point, a radiation bundle delimited by the diaphragms is aligned toward the respectively assigned multi-row detector. The diaphragms are then controlled in at least one embodiment, to delimit and align the two radiation bundles such that these radiation bundles run free from mutual points of intersection, at least in the examination object.

In another inventive variant of at least one embodiment, the currently usual structure of a dual-source CT system having two multi-row detectors arranged on a shared gantry and in each instance focal points centrally facing the multi-row detectors is assumed. A one-sided clipping of the radiation bundle emitted by the focal points to the respective detector with the aid of diaphragms attached in the region of the x-ray tube to approximately half of the opening angle of the radiation bundle in the z-direction can be achieved in that the two radiation bundles no longer intersect. Accordingly, each detector is also only still irradiated partially, when viewed in the z-direction, so that the detector in the peripheral direction continues to be fully used, but only a narrower part in the z-direction is used and read out in the z-direction.

In an advanced variant of at least one embodiment, the focal point of the radiation bundles can be removed in the z-direction from one another for improved separation of the radiation bundle. This results in the usable surface of the detector being widened further. Alternatively, the detectors can also be displaced towards one another in the z-direction or both measures can be combined with one another.

Since, due to the relative displacement of focal point and detector in the z-direction, the incident direction of the individual beams per detector element are changed and possibly are no longer adjusted to the existing scattered radiation grid, the detector can also be tilted simultaneously with the change in the radiation direction of the radiation bundle, so that despite a change in the radiation direction, an optimum alignment is always retained between the detector and the focal point.

Accordingly, the inventor proposes improving an x-ray CT scanning of an examination object with two emitter-detector systems arranged at different angles on a shared gantry of a CT system, wherein each emitter has a focal point and each detector is embodied as a multi-row detector having a scattered radiation grid operating in a two-dimensional manner, and during the scanning process between each focal point and the opposing detector of each emitter-detector system, a radiation bundle diverging in two dimensions and delimited by emitter-side diaphragms is generated. In accordance with at least one embodiment of the invention, the two radiation bundles are to be delimited by the diaphragms respectively such that these radiation bundles are free of mutual points of intersection, at least in the examination object.

In a first embodiment variant, the two focal points, such as is currently usual with a dual-source CT, can run on a shared peripheral line. In current CT systems, this peripheral line lies centrally with respect to the opposing detector. Therefore in the prior art, the opening angle of the beam cone is arranged in the z-direction such that it extends symmetrically with respect to a vertical central radiation between the center point of the detector surface and the opposing focus. With the inventive embodiment of a dual-source CT with two detectors arranged symmetrically in the z-direction having central peripheral lines, which run on a shared circular surface around the system axis, the two radiation bundles are superimposed opposite one another in the z-direction such that the one radiation bundle of the one emitter-detector system is reduced in size from one side toward the center, whereas the other radiation bundle of the other emitter-detector system is reduced in size from the other side toward the center. Accordingly, the usable or used surface reduces on the multi-row detector. Such a procedure is generally possible with currently existing dual-source CT systems, without having to per-form special reconstructions, since such systems in most instances already have a variable diaphragm system for the beam cone.

A central point is here the asymmetric superimposition of the two detectors of a dual tube system with 2D scattered radiation grid for the spatial separation of the rows superimposed in the respective other detector and the reduction in transverse scatter amounts which results therefrom. It is also possible in this way to obtain dual-energy recordings with a high quality in a 2D scattered radiation grid geometry.

Another variant of at least one embodiment of the inventive method resides in the focal points of the two emitter-detector systems being guided onto two separate peripheral lines, wherein the two separate peripheral lines of the focal points then preferably form circular surfaces, which, when viewed in the z-direction, each run offset with respect to the center line of the detectors. This embodiment improves the intersection-free separation of the two beam cones of the two emitter-detector systems. The detector surface, in the case of multi-row detectors arranged on the same peripheral line, can basically be enlarged or an even better separation of the two radiation bundles can be achieved.

The inventor proposes accordingly, in the case of focal points which are not arranged offset in the z-direction, also in one variant of at least one embodiment of the method that the two radiation bundles are delimited in the z-direction such that they only irradiate part of their multi-row detector, preferably only half or a smaller surface. Accordingly, only the irradiated part of the detectors can be used in each instance for determining the radiation attenuation.

It is also advantageous if the focal points are set with respect to their z-coordinates within the respectively irradiated part of the detectors of the associated emitter-detector system.

Furthermore, the two radiation bundles are to radiate their detectors entirely in respect of the peripheral direction. In other words, the additional superimposition of the radiation bundle only takes place in the z-direction, so that the entire opening angle of the radiation bundle is also retained in the peripheral direction, in other words, the row length of the detectors is used entirely.

In a further embodiment variant of the x-ray CT scanning, the inventor proposes aligning at least one of the detectors by tilting the same with respect to the z-axis toward its focus which is offset in the z-direction. Since the detectors have two-dimensional scattered radiation grids, which limit or include the individual beams between the focus and detector element very precisely, a displacement of the focal point in the z-direction can generate a partial shading of the beams on account of the alignment of the scattered radiation grid which is no longer correct. Such a shading can however be prevented if, at the same time as offsetting the focal point in the z-direction, a tilting of the detector element also takes place, which aligns the detector further toward the focal point. If in the process, a mutual offset of the detectors is effected in the z-direction, the radiation bundle separates again even better and less scattered radiation from the respective other emitter-detector system is measured.

The inventor also proposes at least one embodiment directed to a dual-source CT system for scanning an examination object, comprising two emitter-detector systems arranged at different angles on a gantry with, in each instance, at least one x-ray tube, which forms a focal point during operation, which rotates on a peripheral line about a system axis running in the z-direction, and a multi-row detector likewise rotating about the system axis, the detector rows of which run in the peripheral direction, having a scattered radiation grid operating in a two-dimensional manner, wherein, based on the respective focal point, a radiation bundle delimited by the diaphragms is aligned toward the respectively assigned multi-row detector. The diaphragms are then controlled in at least one embodiment, by a device and/or module, such as a controller (which can include a microprocessor for example) and/or control module for example, configured to delimit and align the two radiation bundles such that these radiation bundles run free from mutual points of intersection, at least in the examination object.

In this case provision is made in at least one embodiment of one variant for a focal point which can be positioned differently in the z-direction to be present for at least one multi-row detector. This can be effected for instance in that at least two emitters with a focal point positioned differently in the z-direction are arranged on the gantry for at least one multi-row detector. Alternatively, an emitter with a focal point which can be displaced in the z-direction can also be provided for at least one multi-row detector. Here the focal point can be displaced for instance by displacing the entire x-ray tube itself with the aid of a corresponding apparatus.

Alternatively, the emitter may comprise a rotatable cylindrical anode with an axis of rotation, so that for displacement of the focal point, only the electrons generating the focal point have to strike another point on the cylinder surface of the anode. Only the electron radiation which generates the focal point is therefore displaced in the process. As a result, shifts in weight advantageously do not occur, which would otherwise have to be balanced out in order to prevent imbalances on the gantry.

Furthermore, in a special embodiment, the axis of rotation of the cylindrical anode can be arranged tilted at the same angle relative to the system axis as the associated multi-row detector is tilted, wherein a tilting apparatus is also provided for at least one multi-row detector, said tilting apparatus tilting the multi-row detector relative to the system axis and the gantry. It is herewith possible, when tilting the multi-row detector and simultaneously displacing the focal point, to keep the stereometric relationships between the detector and focal point the same, so that an existing scatter radiation grid furthermore remains optimally aligned toward the focal point.

A displacement apparatus can likewise also be provided for at least one emitter-detector system, said displacement apparatus displacing at least one multi-row detector in the z-direction. Such a displacement apparatus can also be combined with the tilting apparatus.

Alternatively, a displacement apparatus can be provided for at least one emitter-detector system, said displacement apparatus displacing at least one multi-row detector with its focal point in the z-direction. A translation of the detector in the z-direction thus takes place with a simultaneous translation of the focal point, not necessarily the x-ray tube.

Finally, the dual-source CT system can also be embodied such that a displacement apparatus is provided for at least one emitter-detector system, said displacement apparatus displacing at least one emitter-detector system in the z-direction. The at least one emitter-detector system can be positioned individually along the system axis. In a further embodiment, both emitter-detector systems can be positioned individually along the system axis, e.g. in opposed directions. The dual-source CT system incorporates a capability to change the position of the emitter-detector system along the system axis. At least one emitter-detector system can be independently moved along the system axis. If at least one emitter-detector system is displaced, preferably located at a different position along the system axis then the other emitter-detector system, both emitter-detector systems may acquire images in at least partially different planes, wherein the planes are perpendicular to the system axis, preferably in the x-y plane of a Cartesian coordinate system.

Both emitter-detector systems can be used in different planes simultaneously. According to at least one embodiment of the invention, the dual-source CT system enables the acquisition of larger, e.g. axial, coverage. The displacement may be given as offset or shift. The offset may be the same as the shift.

The method may comprise a step of positioning or moving of at least one emitter-detector system. The method may comprise a step of adapting the shift of the emitter-detector systems relative to each other to the pitch. The method may comprise a step of adapting the shift of the emitter-detector systems relative to each other to the requirements of the image acquisition, e.g. bariatric imaging.

To this end, a CT system is developed in at least one embodiment, in which the emitter-detector systems are offset relative to one another in the z-direction to such a degree that, despite using a shared gantry, both emitter-detector systems may run on an identical path or at least acquire data of identical paths through the object, e.g. a shift of 180 degrees. As a result, the appearance of forward scatter and cone beam artefacts may cancel out. Furthermore, in a special embodiment, the offset is selected based on a relative fraction of the detector coverage in the isocenter.

During acquisition, a sequence mode or a helical mode may be used. In sequence mode, a series of images is taken in a timely constant plane without a movement of the patient couch along the system axis. In a further embodiment, several series of images may be taken one after another wherein the patient couch is moved after the end of a previous series and a following series. In helical mode, the patient couch may be moved along the system axis during acquisition. The acquired series of images in helical mode comprises for each emitter-detector system images taken at different positions along the system axis.

Furthermore, in a special embodiment, the acquisition is performed in a sequence mode.

Furthermore, in a special embodiment, the acquisition is performed in a helical mode.

Furthermore, in a special embodiment, the two focal points run onto two separate peripheral lines. The two emitter-detector systems can run onto two separate peripheral lines.

Furthermore, in a special embodiment, the two focal points run onto an identical peripheral line. The two emitter-detector systems can run onto an identical peripheral line.

Furthermore, in a special embodiment, the focal points are set with respect to their z-coordinates within the irradiated part of the detectors of the associated emitter-detector system. In a preferred embodiment, the focal point is set at the same position with respect to the detector area of the associated emitter-detector system.

Furthermore, in a special embodiment, the two radiation bundles each respectively irradiate their respective detectors entirely with respect to the peripheral direction. In a preferred embodiment, the detector areas are irradiated entirely each by the emitter of the associated emitter-detector system. The radiation bundles may comprise mutual points of intersection.

An embodiment of an inventive dual-source CT system 1 is shown in FIG. 1 in a schematic 3D representation. The system 1 essentially includes a gantry housing 6, in which a gantry (not shown explicitly) is disposed, to which are fastened two emitter-detector systems 2, 3 and 4, 5 arranged at different angles about 90° are fastened. Each emitter-detector system includes an x-ray tube 2 or 4 and a multi-row detector 3 or 5 arranged opposite thereto. Controllable diaphragms 2.1 or 4.1 are arranged between the focal points generated in the x-ray tubes 2 or 4 and the measuring field or the examination object 7, here a patient, with which the beam cone originating from the respective focal point can be limited at least in the direction of the system axis 9 (=z direction) for an inventive mode of operation. Aside from the controller of the CT and the data acquisition, the special controller (including a microprocessor, for example) of the diaphragms 2.1, 4.1 and the inventive data acquisition is executed by the control system 10, wherein programs Prg1-Prgn are stored herefor which are executed during operation. In the variant of the inventive CT system 1 shown here, these bring about a mutual superimposition of the two beam cones exclusively in the z-direction, so that the beam cones no longer intersect and only part of the detectors, which is also actually irradiated, is read out. Since no points of intersection are still present between the two beam cones, there are also no more nodes on which scattered radiation from an emitter-detector system could be generated, which runs along the radiation paths in the other emitter-detector system. Accordingly, the scattered radiation portion reduces drastically and artifacts produced by scattered radiation are prevented accordingly.

It is essentially particularly advantageous to embody an embodiment of the inventive method within the scope of a spiral scan, in which the examination object, here a patient 7, is continuously moved through the measuring field during the rotational scanning by the emitter-detector systems with the aid of the patient couch 8. Nevertheless, the invention can also be used in conjunction with a successive circular scanning.

Figure 2:
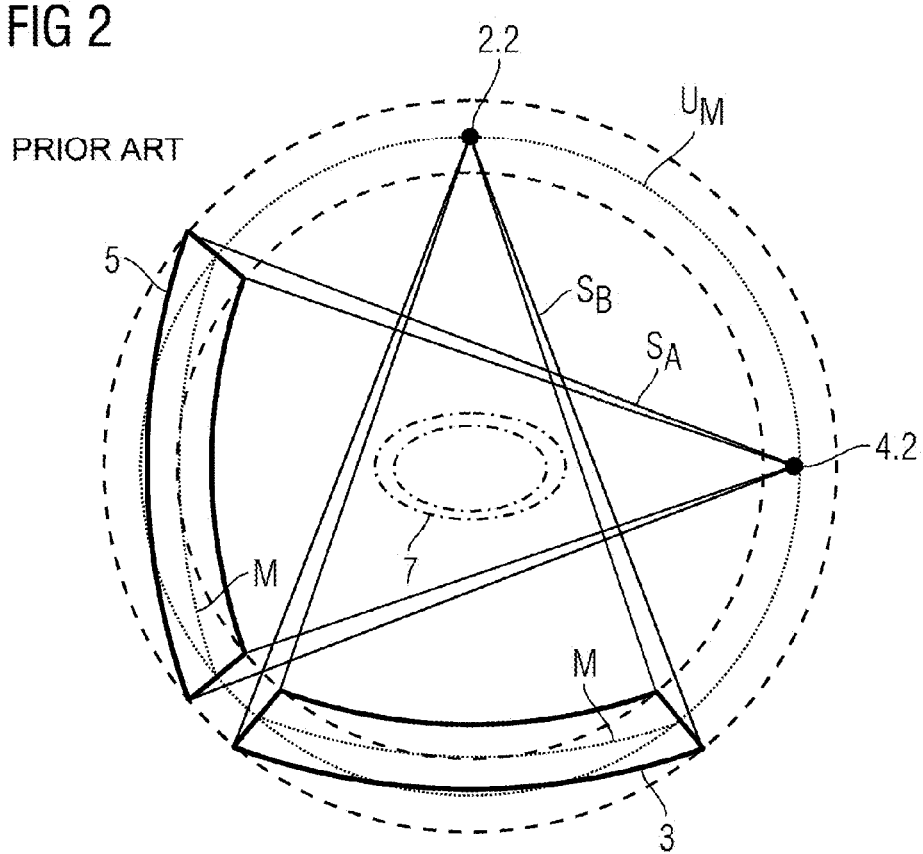
FIG. 2 shows a schematic 3D view of a dual-source CT system according to the prior art from the front.
Figure 3:
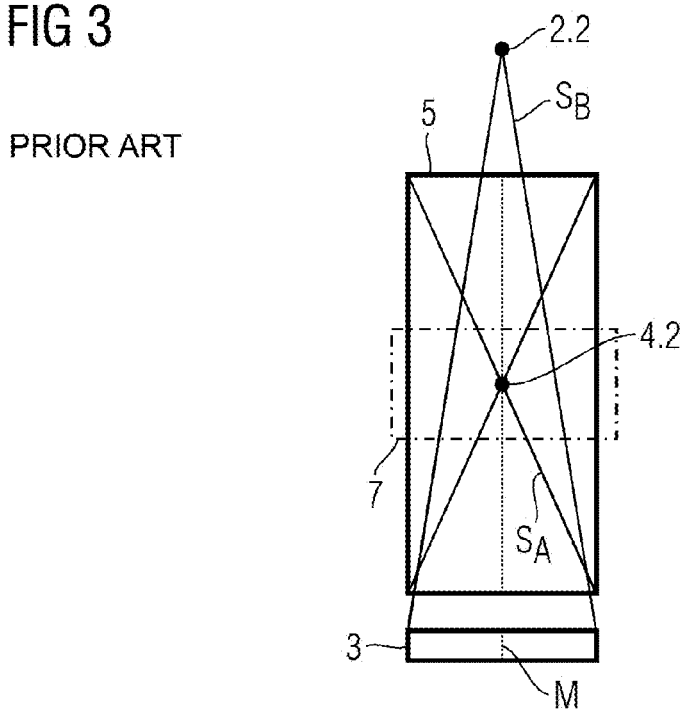
FIG. 3 shows a schematic side view of the CT system from FIG. 2.

In order to explain an embodiment of the invention, a CT system adjusted in accordance with the prior art having emitter-detector systems A and B arranged at different angles on a gantry, is shown in FIGS. 2 and 3, including a multi-row detector 3 and focal point 2.2 or multi-row detector 5 and focal point 4.2 assigned to one another respectively. FIG. 2 shows the emitter-detector systems in a view from the system axis direction and FIG. 3 shows the same in a lateral view at right angles to the system axis. As is apparent, the two beam cones SA and SB intersect, the indices correspond to the emitter-detector systems A and B, in the region of the examination object 7, such that despite an existing, not explicitly indicated—two-dimensional scattered radiation grid, scattered radiation is entered into the respective other emitter-detector system. Both focal points 2.2 and 4.2 move here on a central peripheral line UM. On the circle formed by the peripheral line UM, the center lines M of the detectors 3 and 4 are also disposed.

Figure 4:
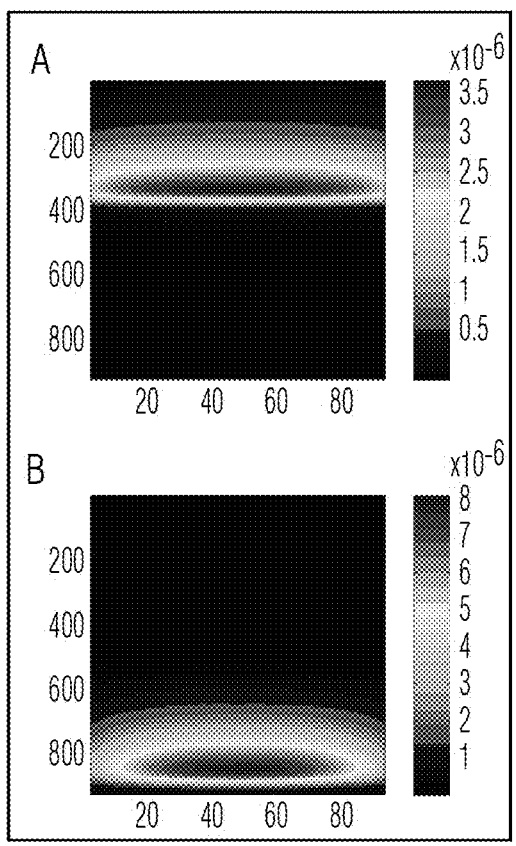
FIG. 4 shows a scattered radiation entry into the emitter-detector systems A+B from the respective other system B+A in a first angle of rotation of the gantry according to FIG. 2.
Figure 5:
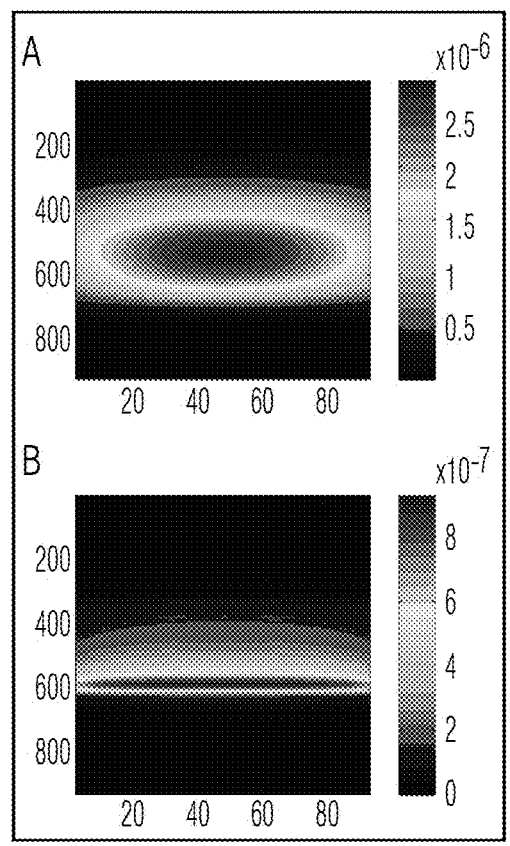
FIG. 5 shows a scattered radiation entry into the emitter-detector systems A+B from the respective other system B+A in a second angle of rotation of the gantry.

The quantity of scattered radiation entered respectively from the other emitter-detector system is clarified in FIGS. 4 and 5, which—recorded at different angles of rotation of the gantry with a non-rotationally symmetrical phantom, indicate the entered scattered radiation intensity on the detectors with 96 lines and 920 rows. The original colored scale of the radiation intensity is indicated in each instance as bars to the right adjacent to the detector. The association with the respective emitter-detector system A or B is likewise indicated adjacent to the detector.

Figure 6:
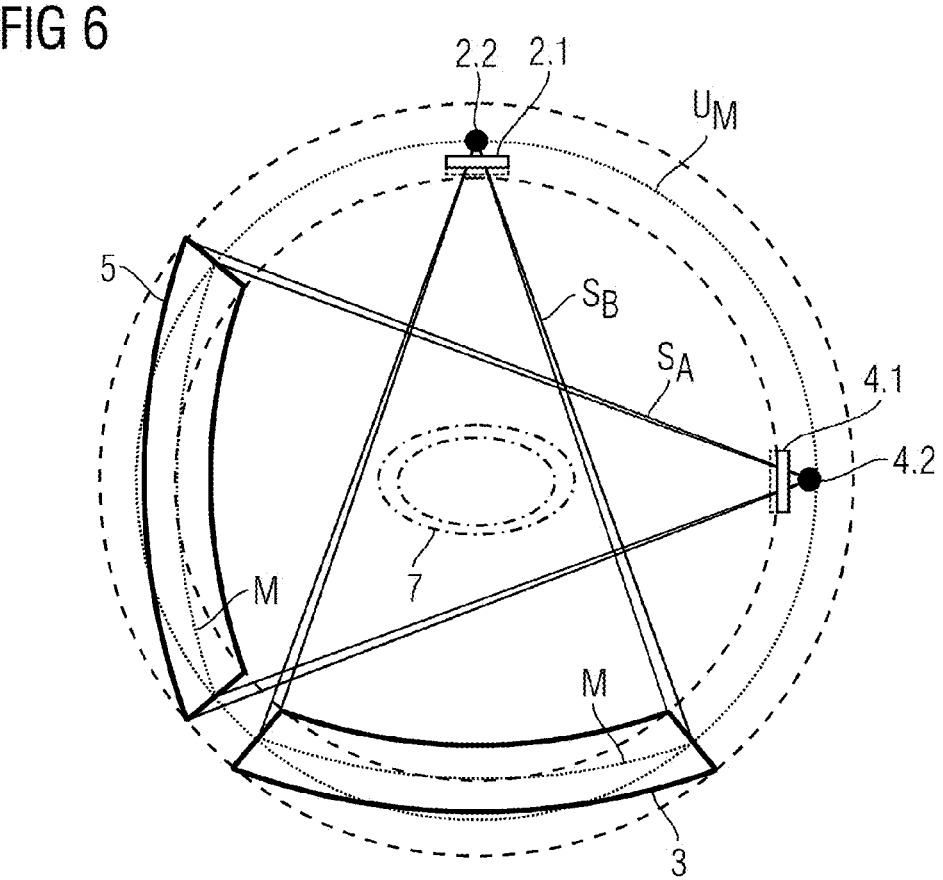
FIG. 6 shows a schematic 3D view of a dual-source CT system with focal points running on a peripheral circle and mutually restricted beam cones.
Figure 7:
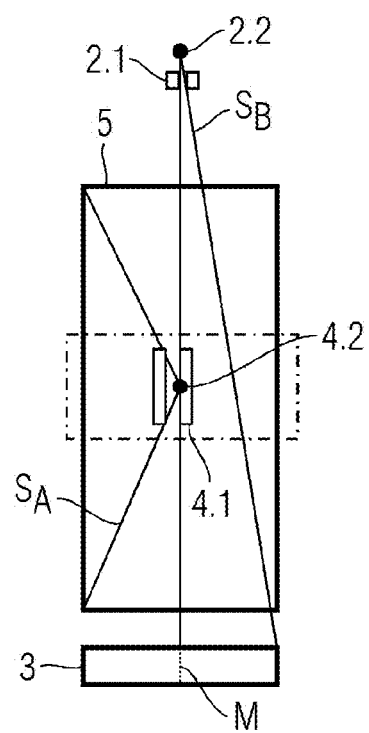
FIG. 7 shows a schematic side view of the CT system from FIG. 6.

In accordance with an embodiment of the invention, the interfering scattered radiation entry can be reduced, by the beam cone being manipulated and arranged such that points of intersection are prevented between the beam cones. To this end, a simple example is show in FIGS. 6 and 7. The representation of the emitter-detector system A and B corresponds to FIGS. 2 and 3, but the two beam cones SA and SB are halved by a corresponding, mutual superimposition in each instance in the z-direction along the peripheral direction, so that each beam cone SA and SB only still irradiates half of its detector 5 or 3. As apparent from FIGS. 6 and 7, the radiation bundles therefore no longer intersect.

Figure 8:
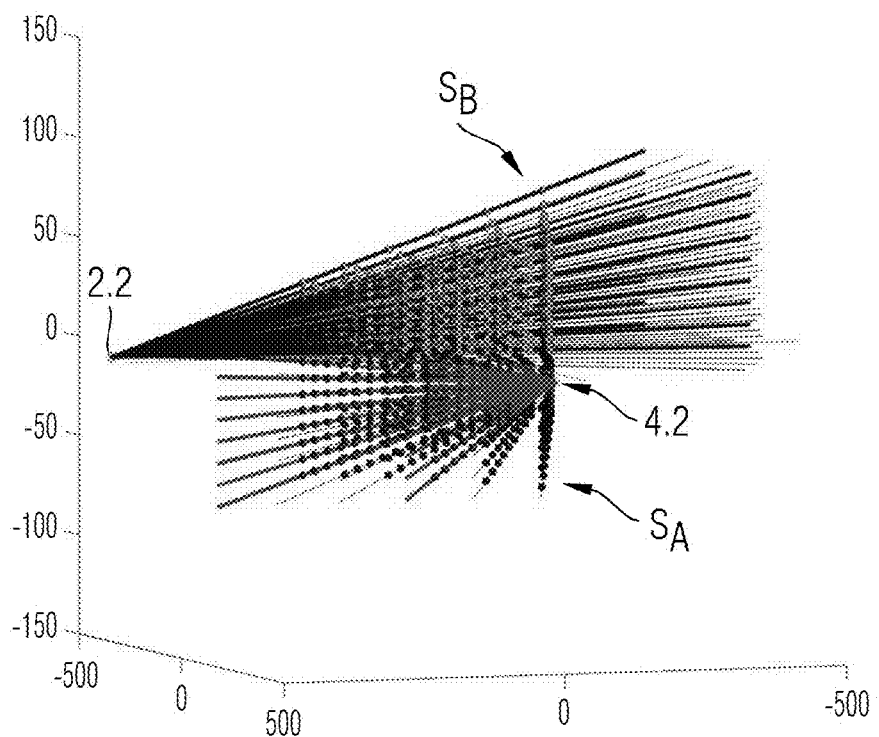
FIG. 8 shows a 3D representation of the radiation bundle from FIG. 6.

Another three-dimensional representation of the two superimposed radiation bundles SA and SB is shown in FIG. 8.

Figure 9:
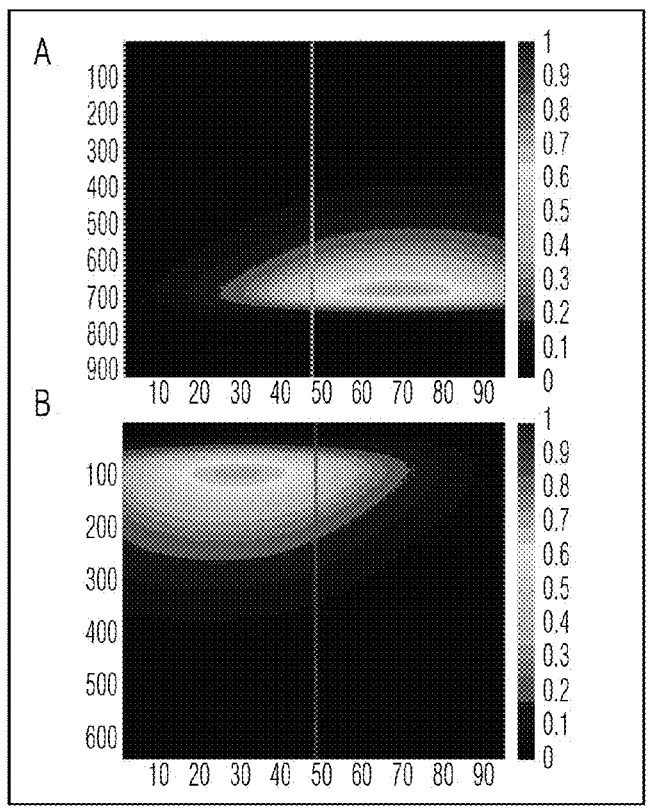
FIG. 9 shows a scattered radiation entry into the emitter-detector systems A+B from the respective other system B+A with a beam cone arrangement according to FIG. 6.

The scattered radiation entry into the respective other detector reduced hereby is shown in FIG. 9, which clarifies the scattered radiation entry according to FIGS. 4 and 5.

Figure 10:
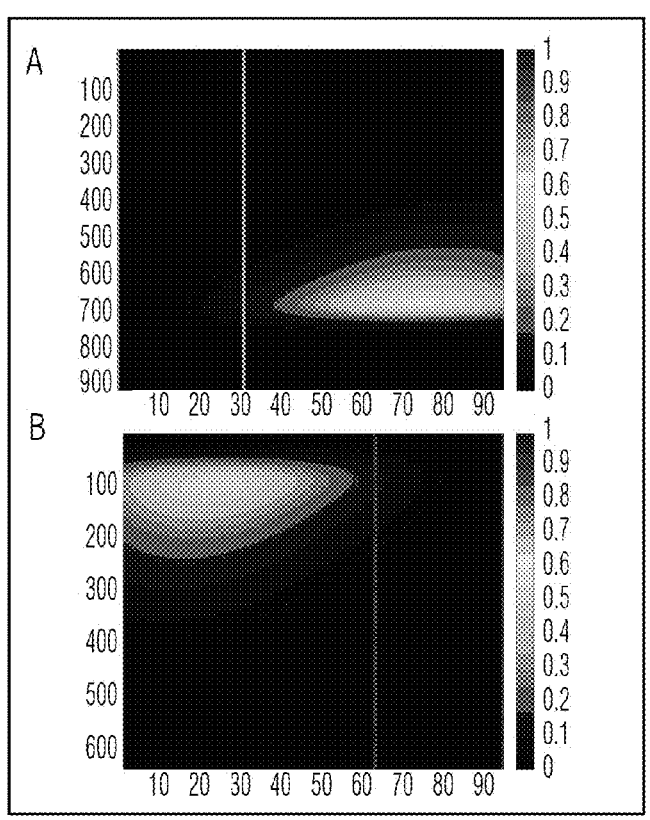
FIG. 10 shows a scattered radiation entry into the emitter-detector systems A+B from the respective other system B+A with a beam cone arrangement according to FIG. 6, nevertheless with a further restriction of the beam cone to a third of the detector surface.

While a superimposition of the beam cone is assumed in FIG. 9 up to the center of the respective detector, FIG. 10 shows the result of a continuous superimposition, so that each detector is only irradiated and used to approximately a third of its width. Accordingly, an improved separation of the radiation bundle is achieved and the proportion of the scattered radiation reverts back to approximately zero in the part of the detector still used respectively for scanning purposes.

Further inventive variants of the embodiment of a dual-source CT system are shown in FIGS. 11 to 14, the aim of which is in each instance to bring about as good a mutual separation of the radiation bundle as possible from the two emitter-detector systems disposed on a gantry.

Figure 11:
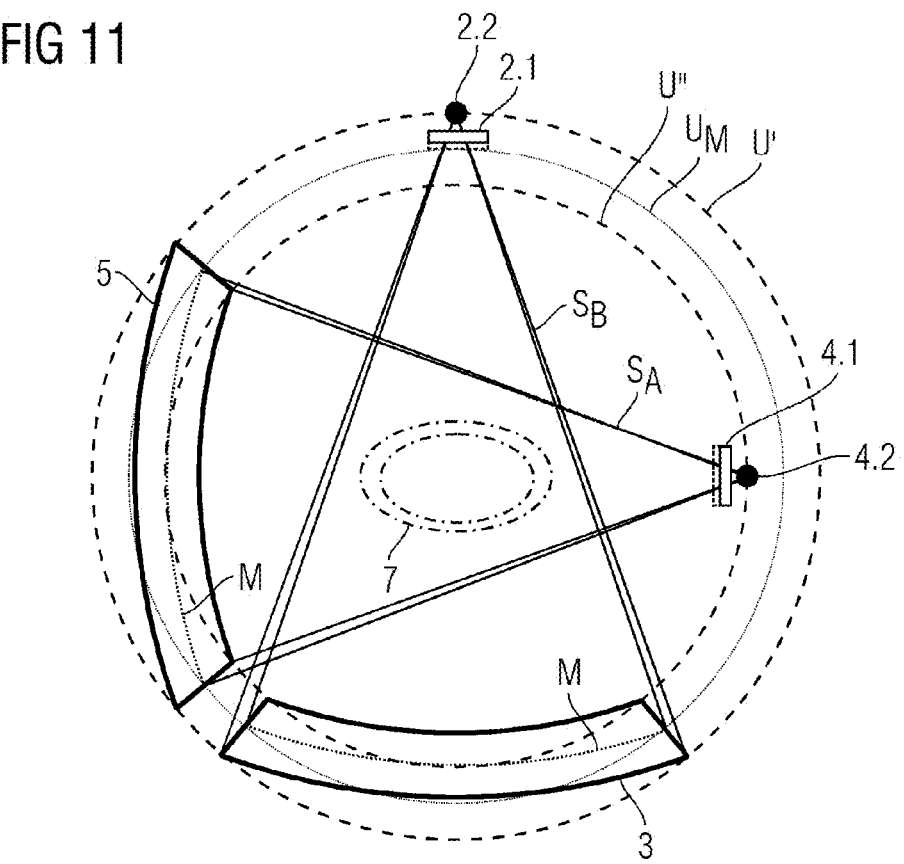
FIG. 11 shows a schematic 3D view of a dual-source CT system with focal points running on different peripheral circles and mutually restricted beam cones.
Figure 12:
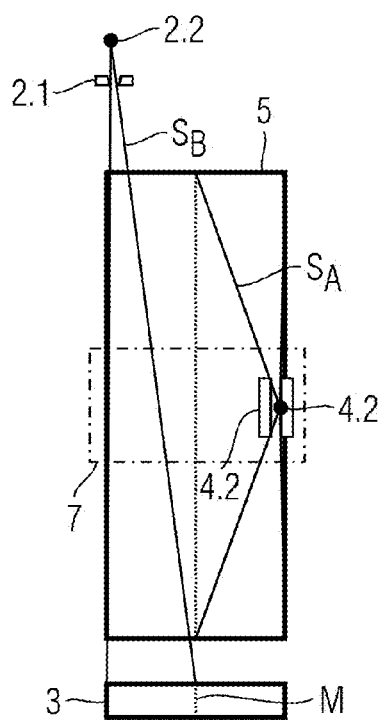
FIG. 12 shows a schematic side view of the CT system from FIG. 11.

FIGS. 11 and 12 show how an improved spatial separation of the beam cone SA and SB can be achieved by an additional z-offset of the focal points 2.2 and 4.2. The two focal points 2.2 and 4.2 move here on the offset peripheral lines U' and U".

Figure 13:
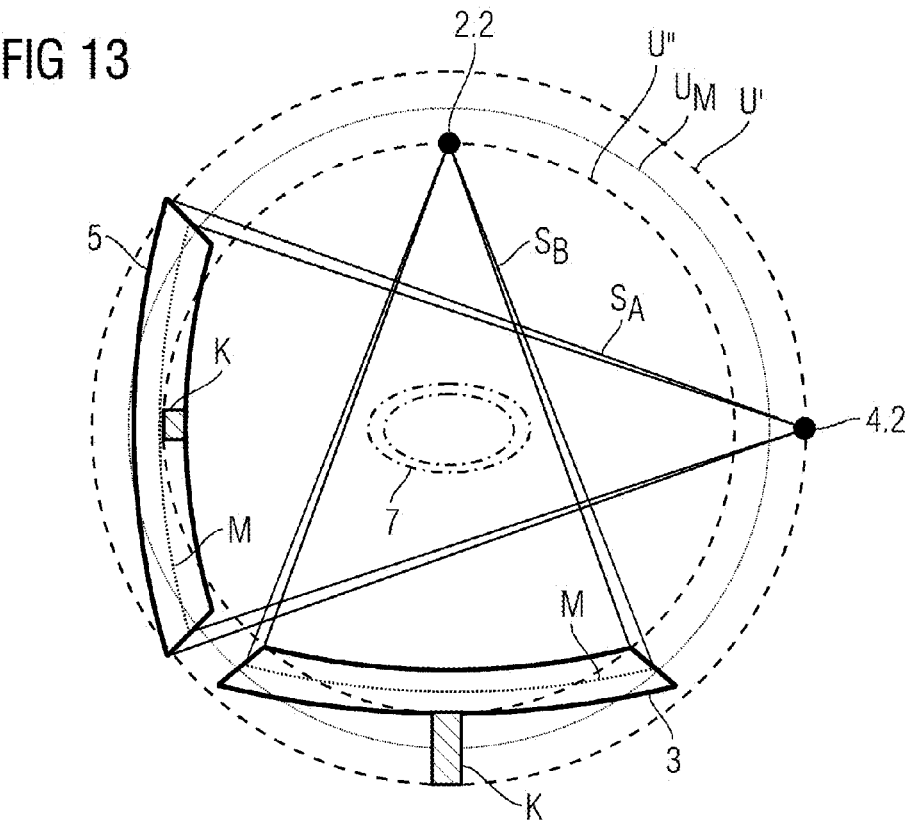
FIG. 13 shows a schematic 3D view of a dual-source CT system according to FIG. 11, nevertheless with tilted detectors.
Figure 14:
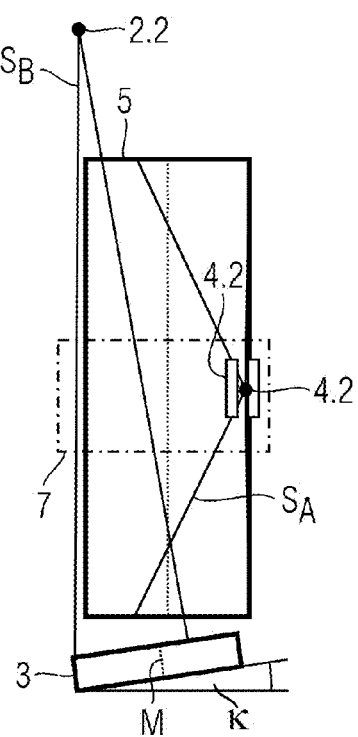
FIG. 14 shows a schematic side view of the CT system from FIG. 13.

In FIGS. 13 and 14, in addition to the z-offset of the focal points, a tilting of the detectors is still shown, wherein an improved alignment of the two-dimensionally acting scattered radiation grid is achieved herewith and the undesired effect of a shading of the beams can be avoided in the scattered radiation grid. The tilting apparatus shown symbolically on the detector 3 is provided with reference character K. The tilting of the detector 3 about the angle K can be particularly easily seen in FIG. 14.

Reference is also made to the superimposition of the two radiation bundles not having to take place at the same time within the meaning of the invention, but it may also be particularly advantageous to execute an uneven superimposition of the radiation bundle. If the two emitter-detector systems are for instance operated inventively with different x-ray energy spectrum, it may be particularly favorable to superimpose the radiation bundle with the higher average radiation energy more significantly than the radiation bundle with the lower average radiation energy. An improved dose weighting can be achieved in this way. By way of example, the radiation bundle with 100 kVp can be assigned to a detector with effectively 54 lines and the radiation bundle with 140 kVp can be assigned to a detector with effectively used 41 lines. A desired dose weighting of 1:1.3 is herewith produced during the scanning process.

Figure 15:
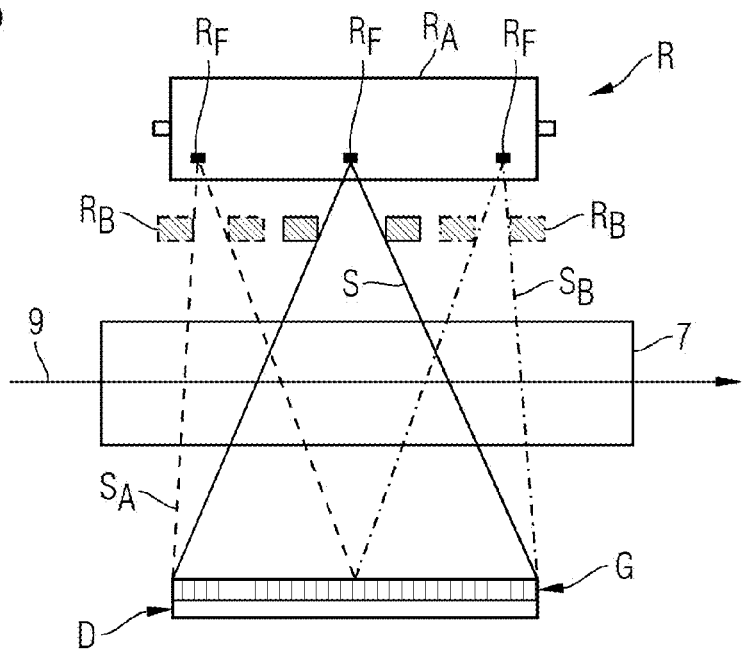
FIG. 15 shows a schematic sectional representation through an emitter-detector system with an x-ray tube having a variable focal point in the z-direction.

As an example of a CT system with a x-ray tube having a variable focal point in the z-direction, FIG. 15 indicates a schematic section through an emitter-detector system along the system axis 9, on which a examination object 7 is shown. In this way the x-ray tube R has a cylindrical anode RA on which, different radiation bundles SA, S, SB are generated depending on the setting of the diaphragms RB and the focal point RF (=focus) on the anode R. As apparent from the Figure, the radiation bundle S can be adjusted for conventional operation such that this irradiates the detector D over the entire z-width, or alternatively a marginal focal point RF can be selected and the diaphragms RB adjusted accordingly such that laterally aligned radiation bundles SA or SB develop, which only partially irradiate the detector D with the scattered radiation grid G arranged thereover and operating in a two-dimensional manner.

Figure 16:
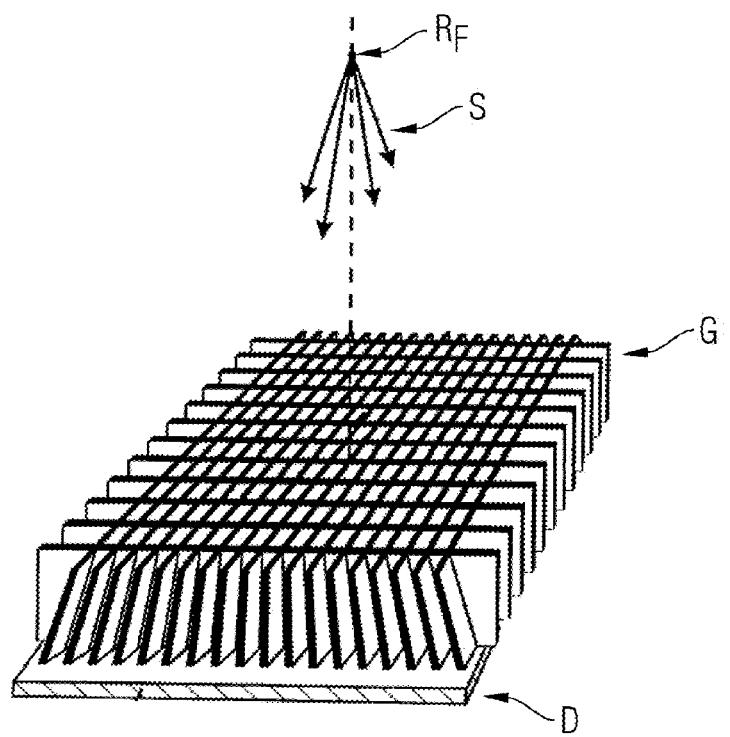
FIG. 16 shows a 3D view of a radiation grid which operates in a two-dimensional manner across a detector.

To clarify the scattered radiation grid G operating in a two-dimensional manner, such a scattered radiation grid is shown in FIG. 16 in a three-dimensional view across a detector D. As apparent, the individual shafts of the radiation grid G are aligned here in accordance with the typical alignment of a radiation bundle S originating from a focal point RF.

Figure 17:
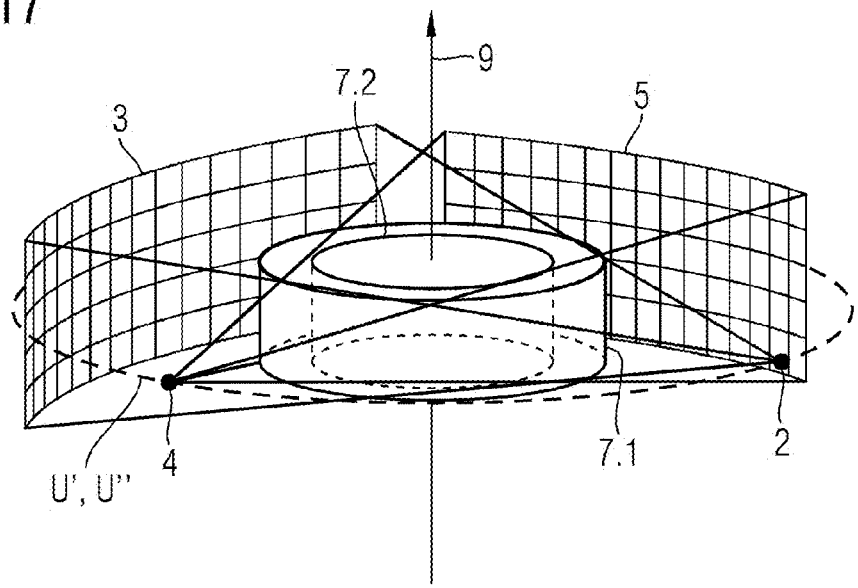
FIG. 17 shows a schematic 3D view of a dual-source CT system according to FIG. 2 in sequence mode.

An embodiment of an inventive dual-source CT system is shown in FIG. 17 in a schematic 3D representation according to FIG. 2 during operation in sequence mode. In this embodiment, the axial coverage is limited to the detector size. The temporal resolution is good. The emitter-detector systems 2, 3, 4, 5 are not displaced in relation to one another along the system axis 9. The focal points of the emitters 2, 4 run on a shared peripheral line U', U". The peripheral line U', U" is a closed path. The fields of view 7.1 and 7.2 represent the acquired volume, e.g. of the patient. The size of the fields of view 7.1 and 7.2 may be different.

Figure 18:
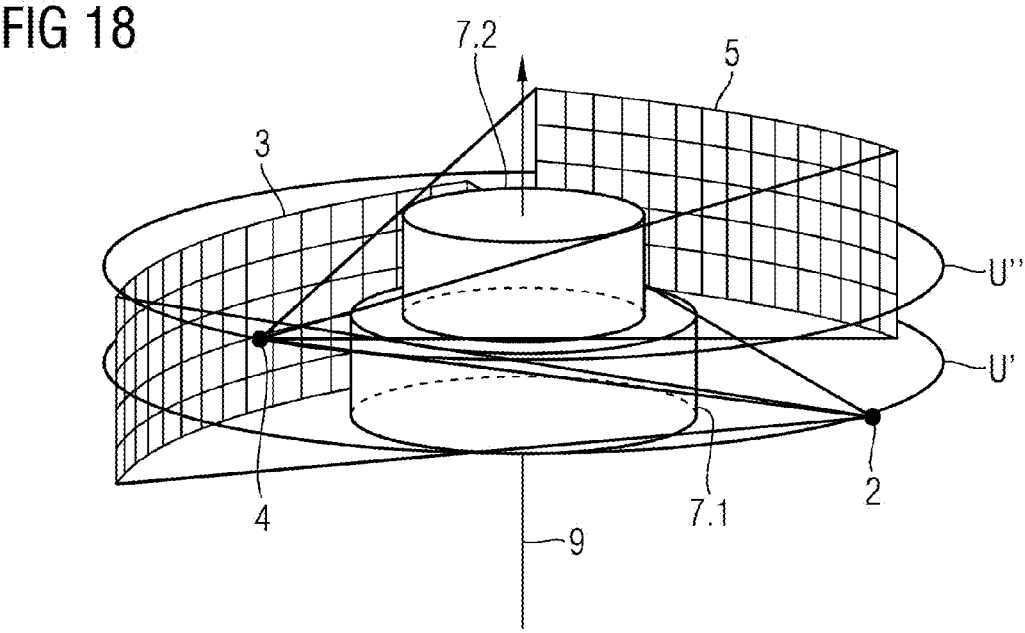
FIG. 18 shows a schematic 3D view of a dual-source CT system with a displaced emitter-detector system B by an offset equal to a relative fraction of the detector coverage in the isocenter of 0.5.

An embodiment of an inventive dual-source CT system is shown in FIG. 18 in a schematic 3D representation. The dual-source CT system comprises a displaced emitter-detector system 4, 5 by an offset equal to a relative fraction of the detector coverage in the isocenter of 0.5 during operation in sequence mode. The shift may be adapted to the desired axial collimation. A wide coverage sequence is enabled by the displaced emitter-detector system 4, 5. A standard temporal resolution is provided. The axial coverage comprises a double detector size. The first emitter-detector systems 2, 3 and the second emitter-detector system 4, 5 are displaced in relation to one another along the system axis 9. The focal point of the emitters 2 runs on a peripheral lines U' which is different to the peripheral line U" on which the emitter 4 runs. The peripherals lines U' and U" are a closed paths.

At least the emitter-detector system B is displaceable. The emitter-detector system may be displaced as a relative fraction of detector coverage in the isocenter, e.g. up to −1 and/or +1. The dual source CT system may be operated e.g. in a dual source helical mode with a pitch e.g. up to 2. The dual source CT system may be operated in a dual energy mode. The dual source system may be operated in a sequence mode or in a helical mode. The pitch is preferably set 1 or 2. The emitter-detector system 4, 5 is mounted at an angle of approximately 90° relative to the emitter-detector system 2, 3. The at least one emitter-detector system is preferably displaced before acquiring a series of images.

Figure 19:
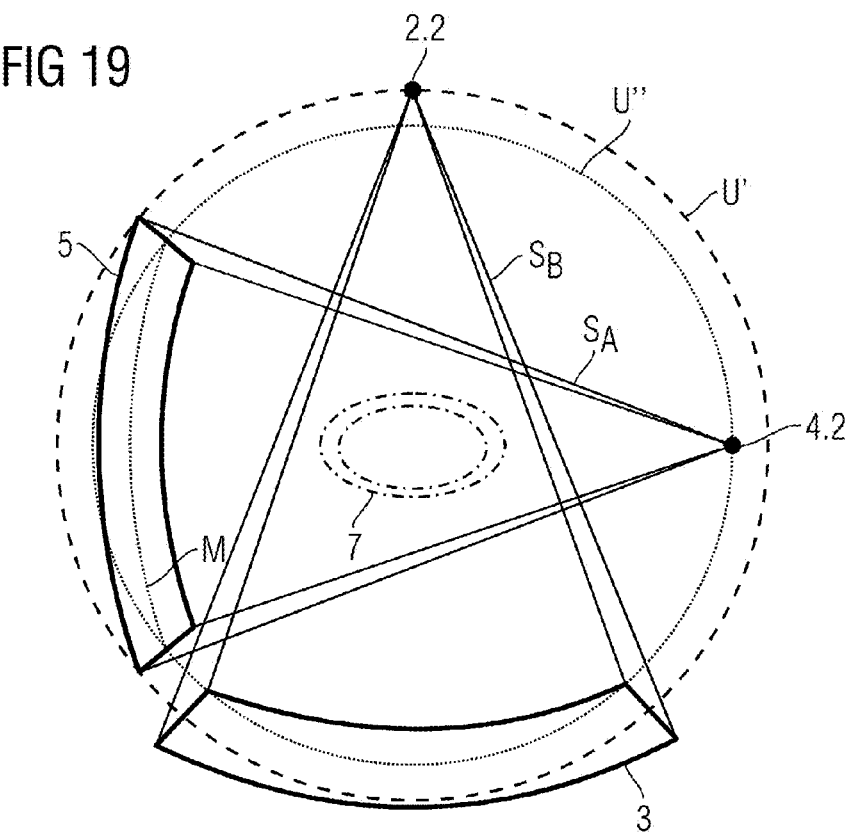
FIG. 19 shows a schematic 3D view of a dual-source CT system with a displaced emitter-detector system of FIG. 18.

An embodiment of an inventive dual-source CT system is shown in FIG. 19 in a schematic 3D representation. The dual-source CT system comprises the displaced emitter-detector system 4, 5 of FIG. 18. The first emitter-detector systems 2, 3 and the second emitter-detector system 4, 5 are displaced in relation to one another along the system axis 9. The focal point 2.2 of the emitter 2 runs on a peripheral line U' which is different to the peripheral line U" on which the focal point 4.2 of the emitter 4 runs. The peripherals lines U' and U" are a closed paths. The radiation bundles or cone beams $S_A$ and $S_B$ comprise mutual points of intersection.

Figure 20:
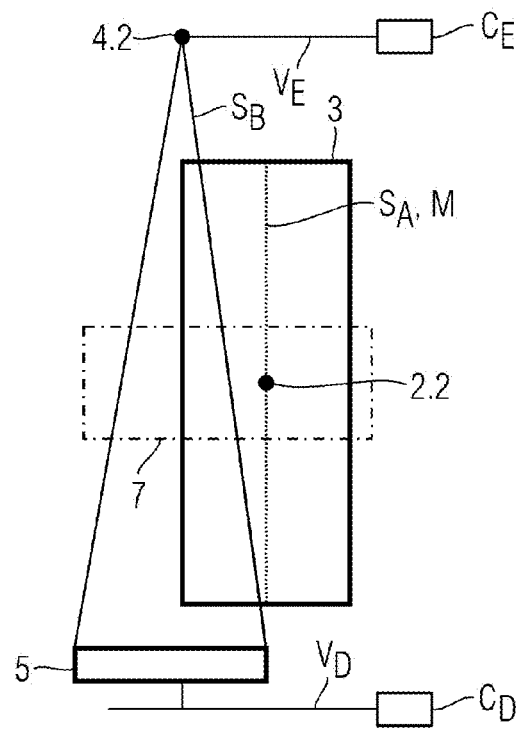
FIG. 20 shows schematic 3D view of a dual-source CT system with a displaced emitter-detector system of FIG. 18.

An embodiment of an inventive dual-source CT system is shown in FIG. 20 in a schematic 3D representation. The dual-source CT system comprises the displaced emitter-detector system 4, 5 of FIG. 18. The emitter with focal point 4.2 is at least mechanically connected to the displacement apparatus $V_E$. The displacement apparatus $V_E$ is controllable by a control unit $C_E$. The displacement apparatus $V_E$ comprises a linear displacement unit. The emitter with the focal point 4.2 is displaceable along the axis of movement of the displacement apparatus $V_E$. The displacement apparatus $V_E$ may comprise an eccentric, slide, rail or any other linear displacement unit. The detector 5 is at least mechanically connected to the displacement apparatus $V_D$. The displacement apparatus $V_D$ is controllable by a control unit $C_D$. The displacement apparatus $V_D$ comprises a linear displacement unit. The detector 5 is displaceable along the axis of movement of the displacement apparatus $V_D$. The displacement apparatus $V_D$ may comprise an eccentric, slide, rail or any other linear displacement unit.

The displacement unit is controlled by the control unit and a computer, which has a memory for corresponding computer programs DPrg1-DPrgn. The computer may be part of the control unit. As alternative, the computer may the computer for controlling the dual-source CT system. An embodiment of the inventive displacement of at least on emitter-detector system can also be executed with such a computer, wherein corresponding program codes are stored in the memory of the computer, which execute the method according to an embodiment of the invention during operation.

Figure 21:
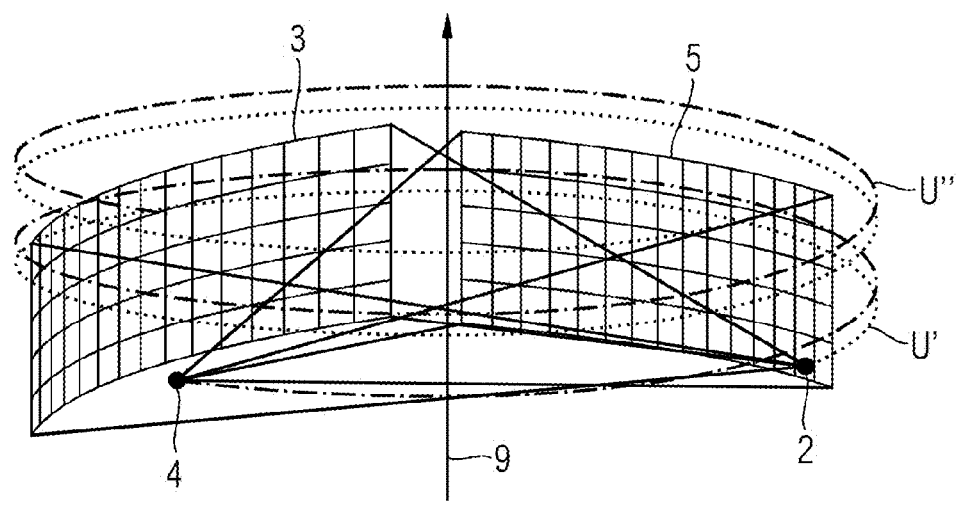
FIG. 21 shows a schematic 3D view of a dual-source CT system according to FIG. 2 in helical mode.

An embodiment of an inventive dual-source CT system is shown in FIG. 21 in a schematic 3D representation according to FIG. 2 during operation in helical mode. Good temporal coherence may be achieved. The acquisition data may suffer from cross-scatter. Contributions to forward scatter effects and artifacts are different for both emitter-detector systems. For bariatric patients, images suffer from artifacts and loss of contrast. The emitter-detector systems 2, 3, 4, 5 are not displaced in relation to one another along the system axis 9. The focal points of the emitters 2, 4 run on a different peripheral lines U' and U" in helical mode. The peripheral lines U' and U" are helical paths.

Any CT helical acquisition may be described as a helical trajectory or path of the emitter-detector system or of the plurality of emitter-detector systems. The helical pitch measures the table feed relative to the coverage of the detector. A dual-source CT system comprises two emitter-detector systems which are mounted within a gantry, or more precisely a rotor, at an offset angle of approximately 90 degrees, preferably 95 degrees. The trajectories of the dual-source CT system can be described by two independent helical paths. By shifting at least one emitter-detector system, the two helical paths are shifted relative to each other, e.g. the distance between the two helical paths. A shift of a first emitter-detector system along the system axis in relation to a second emitter-detector system is beneficial for the reduction of cross scatter.

Figure 22:
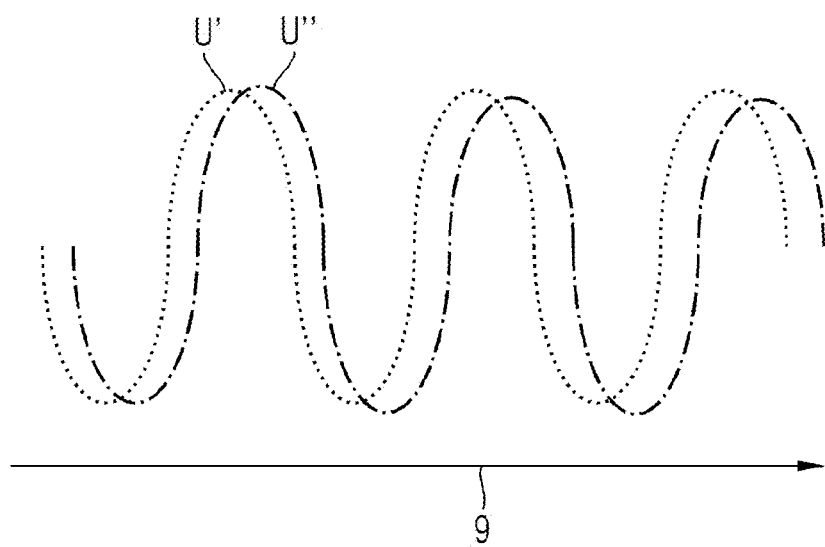
FIG. 22 shows a schematic view of the helical paths of FIG. 21.

In FIG. 22, the helical paths U' and U" of FIG. 21 are shown. The helical paths U' and U" are shifted relative to each other.

Reconstructions of an acquisition in helical mode are mostly not exact in a mathematical sense. The reconstructed images may suffer from artefacts, e.g. cone beam artefacts. Cone beam artefacts comprise low frequency shifts and distortions of the Hounsfield Unit (HU) values in the final image, typically triggered by structures which suddenly change density in direction of the system axis (e.g. vertebra). Other possible artefacts are due to scattered radiation. Forward scatter effects may arise due to scattered radiation of an emitter, e.g. emitter 4, passing the object in a scattered way which is detected by the detector, e.g. detector 5, wherein the emitter and the detector are comprised by the same emitter-detector system. The event is not registered in the expected detector element of detector A, instead the event is registered in an unexpected detector element within the detector. The event would be expected at the detector element which is hit after passing the object along a straight path. In contrast, cross scatter radiation can comprise scattered radiation emitted by emitter A which passes the object and is registered in detector B due to scatter effects, e.g. within the object or patient. If both emitter-detector systems are operated at the same time in helical mode, the both emitter-detector systems each cause independent artefacts.

A well-known effect which is triggered by forward scatter is the quick-scan artefact in cardiac images in which HU instabilities for low frequencies occur. The quick-scan artefacts may be due to the fact that only 180 degrees of data are used for reconstruction. The start and stop angle of the data interval is arbitrary since it may depend on the ECG signal. Furthermore, the shape of the patient along the image plane, which may be perpendicular to the system axis, is usually elliptical. The rotational symmetry is broken. HU values can vary due to the differences in forward scatter amplitude depending on the data contribution to the final image. A dual energy helical acquisition with a relative high pitch, e.g. 1.2 to 1.5, may exhibit quick-scan artefacts due to the amount of data contributing to each image, e.g. an angular range of data of 180 degrees acquired at a pitch of 1.5. The evaluation of the images from both detectors may be influenced. If the offset between the two emitter-detector systems equals to a relative fraction of the detector coverage in the isocenter of 0.25 or −0.75, each image of both detectors is based on the same angular range of projections. The images may exhibit the same identical forward scatter contributions which may cancel out in later processing.

According to an embodiment of the invention, the two emitter-detector systems A+B are operated at an offset along the system axis matching their system angle, which is the angle between both emitter-detector systems A and B. If the emitter-detector system A is mounted at 90 degrees and the emitter-detector system B is mounted at 360 degrees, the offset along the system axis may be equal to a relative fraction of the detector coverage in the isocenter of 0.25 or equivalently of −0.75. In this embodiment, only artefacts of a single system are present and appear reduced compared to the standard operation mode without offset along the system axis. In general, a first emitter-detector system is mounted at an angle x1 and a second emitter-detector system is mounted at an angle x2, the displacement noted as relative fraction of the detector coverage in the isocenter may equal to $x1/x2+n$, wherein $n \in \mathbb{Z}$, in order to match the offset along the system to the system angle resulting in identical projections. The system angle may be written as difference between the angles x1 and x2. In the above example embodiment, where x1 equals 90 degrees and x2 equals, the system angle equals to 90 degrees.

Figure 23:
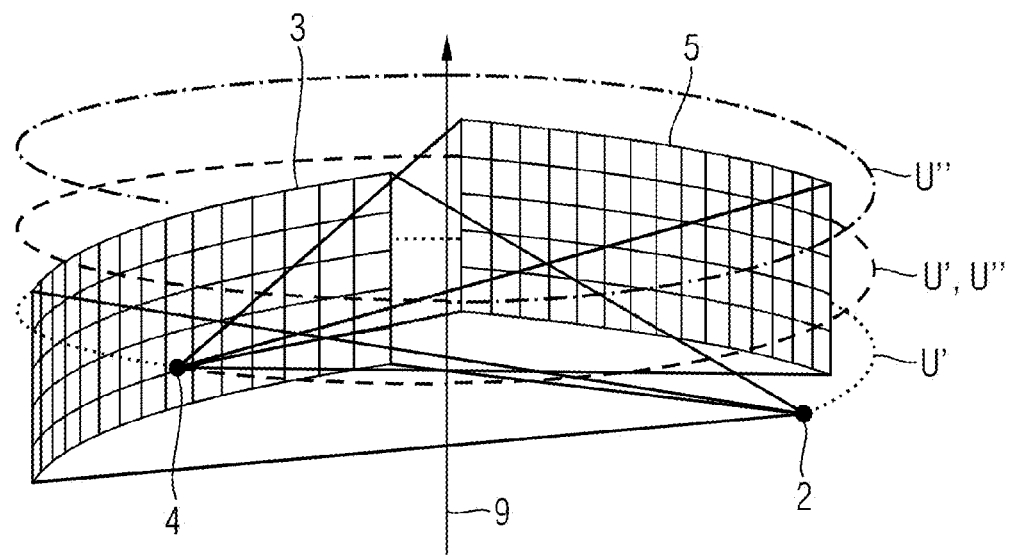
FIG. 23 shows a schematic 3D view of a dual-source CT system with a displaced emitter-detector system B by an offset equal to a relative fraction of the detector coverage in the isocenter of 0.25 in a helical mode.

An embodiment of an inventive dual-source CT system is shown in FIG. 23 in a schematic 3D representation. The dual-source CT system comprises a displaced emitter-detector system 4, 5 by an offset equal to a relative fraction of the detector coverage in the isocenter of 0.25 during operation in a helical mode. The shift of the emitter-detector system 4, 5 is adapted to the spiral or helical pitch. Both emitter-detector systems 2,3,4,5 rotate along the identical helical path U', U". An improved dual energy helical acquisition is achieved. In dual energy acquisitions, the emitter 2 is operated at a different tube voltage than emitter 4. A dual energy acquisition can be understood as a kind of subtraction of the two images of both emitter-detector systems, one image acquired with a first emitter-detector system and another image acquired with a second emitter-detector system. Systematic effects which are present in both images and which are not identical will show up and may be identified.

If the systematic effects or artefacts are identical, they cancel out. This canceling may be at least true for cone beam artefacts. This canceling may also be true for forward scatter radiation contributions. The temporal coherence is reduced. The cross-scatter is reduced. The contributions to forward scatter effects and artifacts are identical for both detector-emitter systems. The image results may be improved, if motion is negligible. Cone beam artefacts may be reduced.

Figure 24:
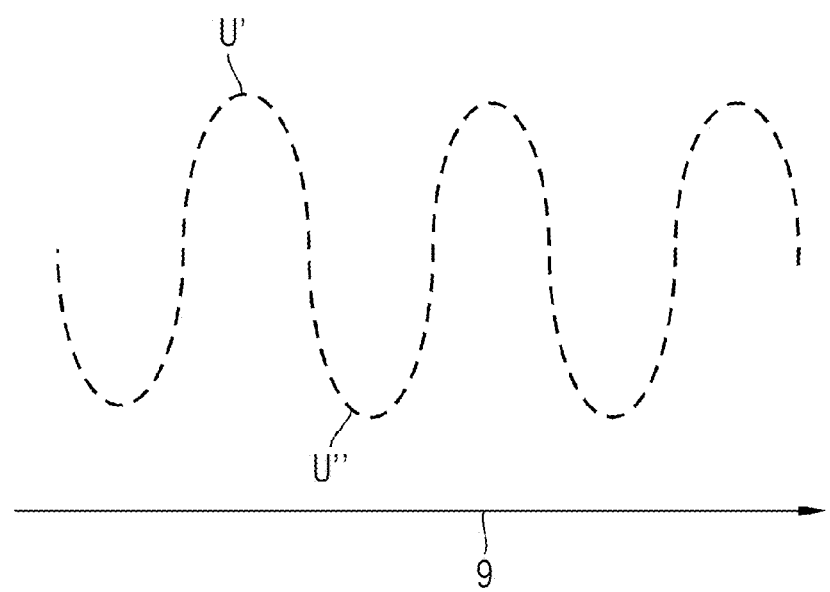
FIG. 24 shows a schematic view of the helical paths of FIG. 23.

In FIG. 24, the helical path U', U'' of FIG. 23 is shown. The helical paths U' and U'' are identical. Both paths U' and U'' are identical within a certain range along the system axis 9.

Figure 25:
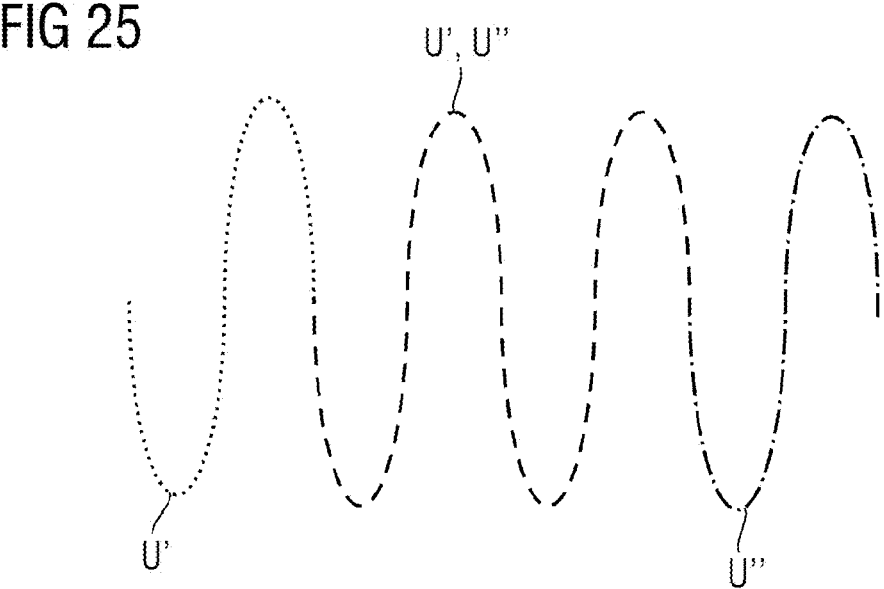
FIG. 25 shows a schematic view of helical paths according to an alternative embodiment of a displaced emitter-detector system B by an offset equal to a relative fraction of the detector coverage in the isocenter of −0.75.

The helical paths of another embodiment of an inventive dual-source CT system are shown in FIG. 25. The helical paths are shown along the system axis. The dual-source CT system comprises a displaced emitter-detector system 4, 5 by an offset equal to a relative fraction of the detector coverage in the isocenter of −0.75 during operation in a helical mode. Both paths U' and U'' are identical within a certain range along the system axis 9.

Figure 26:
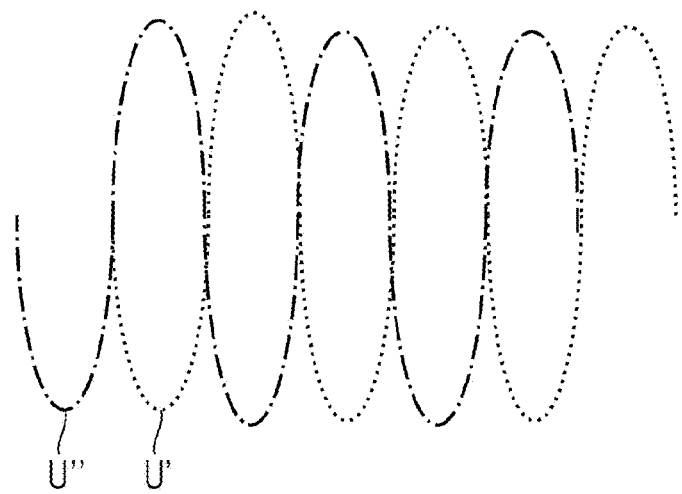
FIG. 26 shows a schematic view of helical paths of an alternative embodiment of a displaced emitter-detector system B by an offset equal to a relative fraction of the detector coverage in the isocenter of 0.75.

The helical paths of another embodiment of an inventive dual-source CT system are shown in FIG. 26. The helical paths are shown along the system axis. The dual-source CT system comprises a displaced emitter-detector system B by an offset equal to a relative fraction of the detector coverage in the isocenter of 0.75 during operation in a helical mode. The offset of 0.75 can be beneficial as the two emitter-detector systems run, preferably exactly, opposed to each other. A projection at an angle x is acquired with the emitter-detector system A while another projection at an angle x+180° is acquired with the other emitter-detector system B. For both emitter-detector systems the projection path is the same path, e.g. from the emitter to the detector, whereas the direction of propagation of the x-rays is diametrically opposite. In general, a first emitter-detector system is mounted at an angle x1 and a second emitter-detector system is mounted at an angle x2, the displacement noted as relative fraction of the detector coverage in the isocenter may equal to x1/x2+n+0.5, wherein n∈$\mathbb{Z}$, in order to match the offset along the system to the system angle resulting in diametrically opposing projections.

Figure 27:
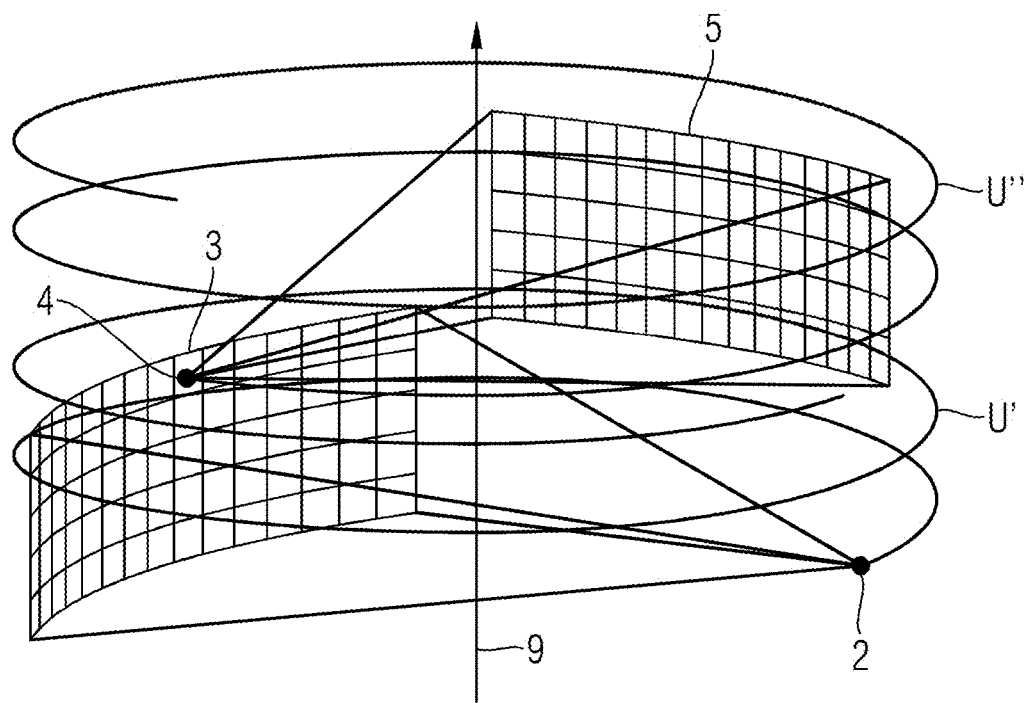
FIG. 27 shows a schematic 3D view of a dual-source CT system with a displaced emitter-detector system B by an offset equal to a relative fraction of the detector coverage in the isocenter of 1 in a helical mode.

An embodiment of an inventive dual-source CT system is shown in FIG. 27 in a schematic 3D representation. The dual-source CT system comprises a displaced emitter-detector system 4, 5 by an offset equal to a relative fraction of the detector coverage in the isocenter of 1 during operation in a helical mode. Bariatric imaging may be improved. A large shift of approximately one detector width may prevent from cross-scatter. The large shift enables a wide coverage. The temporal coherence is lower. The cross-scatter is reduced which provides improved contrast, if motion is negligible. The focal points of the emitters 2, 4 run on a different peripheral lines U' and U'' in helical mode. The peripheral lines U' and U'' are helical paths. The radiation bundles emitted by the emitters 2, 4 are free of mutual points of intersection, at least in the examination object.

Figure 28:
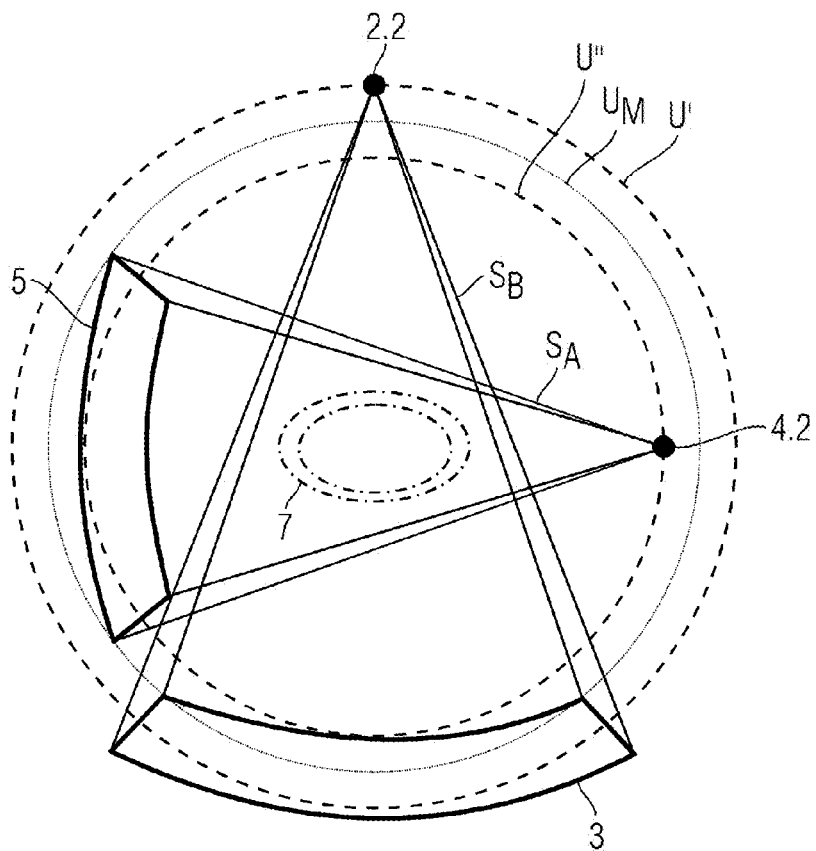
FIG. 28 shows a schematic 3D view of a dual-source CT system with a displaced emitter-detector system of FIG. 27.

In FIG. 28, a schematic 3D view of a dual-source CT system with a displaced emitter-detector system B of FIG. 27 is shown. The dual-source CT system comprises the displaced emitter-detector system 4, 5 of FIG. 18. The first emitter-detector systems 2, 3 and the second emitter-detector system 4, 5 are displaced in relation to one another along the system axis 9. The focal point 2.2 of the emitter 2 runs on a peripheral line U' which is different to the peripheral line U'' on which the focal point 4.2 of the emitter 4 runs. The peripherals lines U' and U'' are a helical paths. The helical paths U' and U'' are shifted relative to each other. The radiation bundles or cone beams $S_A$ and $S_B$ are free of mutual points of intersection. The central peripheral line $U_M$ may be a peripheral line on which the edges of both detectors run. As alternative, both emitter-detector systems may be displaced, e.g. by an offset equal to a relative fraction of the detector coverage in the isocenter of 0.5 or −0.5, respectively. In this alternative embodiment, the central peripheral line $U_M$ is located along the trajectory of the middle line of the detector or the focal point of a non-shifted emitter-detector system.

Figure 29:
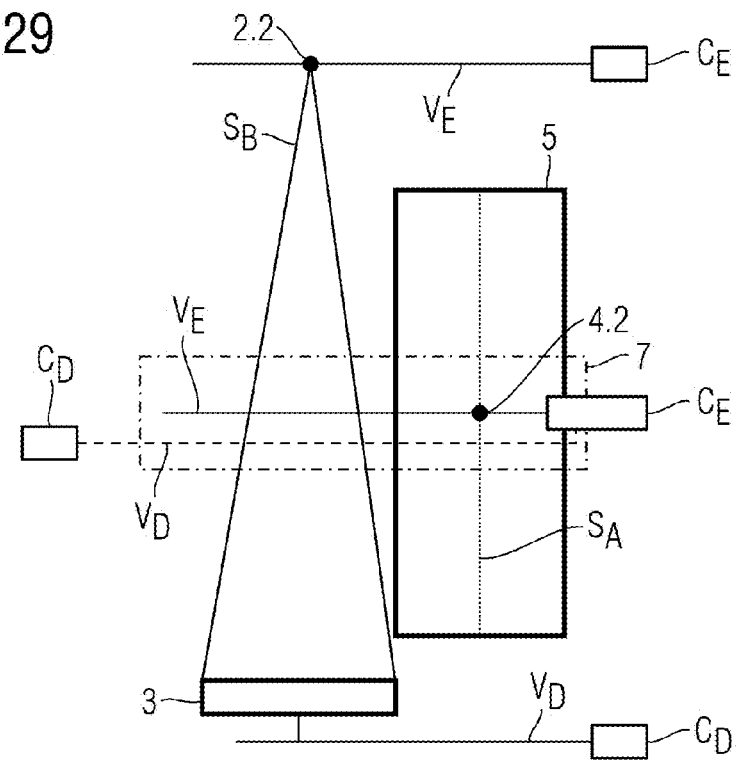
FIG. 29 shows a schematic 3D view of a dual-source CT system with two displaceable emitter-detector systems.

In FIG. 29, a schematic 3D view of a further embodiment of a dual-source CT system with two displaceable emitter-detector systems A and B is shown. The emitters with focal point 2.2 or 4.2, respectively, are each at least mechanically connected to a displacement apparatus $V_E$. The displacement apparatus $V_E$ is controllable by a control unit $C_E$. The displacement apparatus $V_E$ comprises a linear displacement unit. The emitters with the focal point 2.2 or 4.2, respectively, are each independently displaceable along the axis of movement of the displacement apparatus $V_E$. The axis of movement of the displacement apparatus $V_E$, $V_D$ is preferably parallel to the system axis. The displacement apparatus $V_E$ may comprise an eccentric, slide, rail or any other linear displacement unit. The detectors 3 and 5 are each at least mechanically connected to a displacement apparatus $V_D$. The displacement apparatus $V_D$ is controllable by a control unit $C_D$. The displacement apparatus $V_D$ comprises a linear displacement unit. The detectors 3 and 5 are displaceable along the axis of movement of the displacement apparatus $V_D$. The displacement apparatus $V_D$ may comprise an eccentric, slide, rail or any other linear displacement unit.

Figure 30:
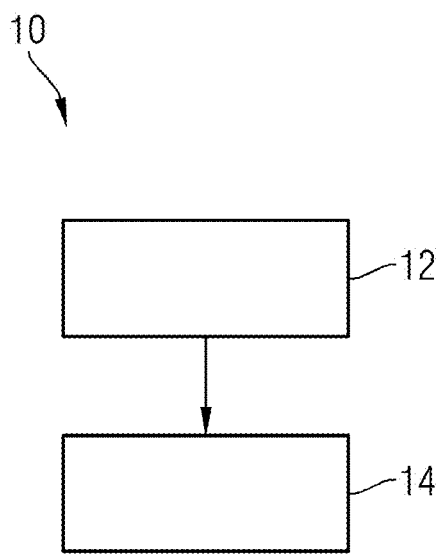
FIG. 30 shows a schematic presentation of the method of using a dual-source CT system according to the invention.

In FIG. 30, a schematic presentation of the method 10 of using a dual-source CT system according to the invention is shown. A method of X-ray CT scanning of an examination object using two emitter-detector systems arranged at different angles on a shared gantry of a CT system, each of the two emitters including a focal point and each of the two detectors being embodied as a multi-row detector with a scattered radiation grid operating in a two-dimensional manner. In a first step 12, an offset, e.g. in terms of a relative fraction of the detector coverage in the isocenter, is selected. In particular, the offset is selected as a relative fraction of the detector coverage in the isocenter. The selected offset may be sent to the control units $C_D$, $C_E$. The selected offset is set, e.g. within a register of the control units $C_D$, $C_E$. The emitter-detector system A and/or B is moved by the offset along the system axis by the displacement apparatuses $V_E$, $V_D$. The control units $C_D$, $C_E$ can control the displacement apparatus $V_D$, $V_E$ and the movement of the linear displacement unit. In a second step 14, an acquisition is performed, e.g. in sequence or helical mode, with at least one displaced emitter-detector system. During the acquisition, a series of images or projections is taken during rotation of the emitter-detector systems. The second step 14 comprises generating, during the scanning process between each of the respective focal points and an opposing one of the two detectors of each of the two emitter-detector systems, a radiation bundle diverging in two dimensions.

It is therefore proposed overall with embodiments of the invention, within the scope of an x-ray CT scan with a dual-source system, to delimit the two radiation bundles by diaphragms such that these radiation bundles, at least in the examination object, are free of mutual points of intersection. Accordingly, a dual-source CT system is also proposed, which includes at least one device/module to control the radiation-delimiting diaphragms, which delimit and align the two radiation bundles such that these radiation bundles, at least in the examination object, run freely from mutual points of intersection.

Although the invention has been illustrated and described in detail on the basis of the preferred example embodiment, the invention is not limited by the disclosed examples and other variations can be derived herefrom by the person skilled in the art, without departing from the scope of protection of the invention.

What is claimed is:

1. A method of X-ray CT scanning of an examination object using two emitter-detector systems arranged at different angles on a shared gantry of a CT system, each of the two emitters including a focal point and each of the two detectors being embodied as a multi-row detector with a scattered radiation grid operating in a two-dimensional manner, the method comprising:

selecting an offset corresponding to a shift of the two emitter-detector systems relative to one another and moving at least one emitter-detector system by the offset along a system axis, generating, during the scanning process between each of the respective focal points and an opposing one of the two detectors of each of the two emitter-detector systems, a radiation bundle diverging in two dimensions and acquiring an image for each of the two detectors, wherein the focal points are set with respect to their z-coordinates within the irradiated part of the detectors of the associated emitter-detector system, wherein the offset of the two emitter-detector systems in the z-direction is selected based on a relative fraction of the detector coverage in the isocenter.

2. The method of X-ray CT scanning of claim 1, wherein the acquisition is performed in a sequence mode.

3. The method of X-ray CT scanning of claim 1, wherein the acquisition is performed in a helical mode.

4. The method of X-ray CT scanning of claim 1, wherein the two focal points run onto an identical peripheral line.

5. The method of X-ray CT scanning of claim 1, wherein the two focal points run onto two separate peripheral lines.

6. The method of X-ray CT scanning of claim 1, wherein the two radiation bundles each respectively irradiate their respective detectors entirely with respect to the peripheral direction.

7. A dual-source CT system for scanning an examination object, comprising:

two emitter-detector systems, arranged at different angles on a gantry, each including
at least one x-ray tube which forms a respective focal point during operation and which is configured to rotate on a peripheral line about a system axis running in the z-direction, and
a multi-row detector, configured to rotate about the system axis, detector rows of the multi-row detector being configured to run in the peripheral direction, the multi-row detector including a scattered radiation grid configured to operate in a two-dimensional manner, wherein, a displacement apparatus is provided for at least one emitter-detector system, which is configured to displace at least one emitter-detector system in the z-direction, wherein each respective focal point is set with respect to its z-coordinate within the irradiated part of the detectors of the associated emitter-detector system; and
a controller configured to select an offset of the two emitter-detector systems in the z-direction based on a relative fraction of the detector coverage in the isocenter.

8. The dual-source CT system of claim 7, wherein at least one displacement apparatus is provided for at least one emitter-detector system, which is configured to displace the at least one emitter-detector system in the z-direction.

9. The dual-source CT system of claim 7, further comprising a control unit for controlling the displacement apparatus.

10. The method of X-ray CT scanning of claim 1, wherein the offset is adapted to the pitch.

11. The method of X-ray CT scanning of claim 1, wherein the offset equals to a relative fraction of the detector coverage in the isocenter of 0.25 during operation.

12. The method of X-ray CT scanning of claim 1, wherein the offset equals to a relative fraction of the detector coverage in the isocenter of 0.75 during operation.

13. The method of X-ray CT scanning of claim 1, wherein the offset equals to a relative fraction of the detector coverage in the isocenter of −0.75 during operation.

14. The method of X-ray CT scanning of claim 1, wherein the offset equals to a relative fraction of the detector coverage in the isocenter of 1 during operation.

* * * * *